United States Patent
Houser et al.

(10) Patent No.: US 6,726,696 B1
(45) Date of Patent: Apr. 27, 2004

(54) PATCHES AND COLLARS FOR MEDICAL APPLICATIONS AND METHODS OF USE

(75) Inventors: Russell A. Houser, Livermore, CA (US); William D. Hare, Bethesda, MD (US)

(73) Assignee: Advanced Catheter Engineering, Inc., Livermore, CA (US)

(*) Notice: Subject to any disclaimer, the term of this patent is extended or adjusted under 35 U.S.C. 154(b) by 0 days.

(21) Appl. No.: 10/183,396

(22) Filed: Jun. 28, 2002

Related U.S. Application Data

(63) Continuation-in-part of application No. 10/127,714, filed on Apr. 23, 2002.
(60) Provisional application No. 60/286,269, filed on Apr. 24, 2001, provisional application No. 60/300,892, filed on Jun. 25, 2001, and provisional application No. 60/302,255, filed on Jun. 28, 2001.

(51) Int. Cl.⁷ .................................................. A61B 17/04
(52) U.S. Cl. ....................................... 606/151; 606/213
(58) Field of Search ............................... 606/151, 213; 602/48, 76

(56) References Cited

U.S. PATENT DOCUMENTS

| | | | | |
|---|---|---|---|---|
| 5,116,357 A | * | 5/1992 | Eberbach .................... 606/213 |
| 5,333,624 A | * | 8/1994 | Tovey .......................... 128/897 |
| 5,370,650 A | * | 12/1994 | Tovey et al. ................ 606/151 |
| 5,405,360 A | * | 4/1995 | Tovey .......................... 606/151 |
| 6,042,592 A | * | 3/2000 | Schmitt ....................... 606/151 |
| 6,258,113 B1 | * | 7/2001 | Adams et al. .............. 606/192 |
| 6,375,662 B1 | * | 4/2002 | Schmitt ....................... 606/151 |

* cited by examiner

*Primary Examiner*—Gary Jackson

(57) ABSTRACT

The invention relates to applying a patch to a tissue surface within a mammalian body that includes retaining the patch to a deployment device, advancing the deployment device to the tissue surface, pressing the patch against the tissue surface, and manipulating the deployment device to separate the deployment device from the patch and leave the patch against the tissue surface. The patch includes at least one layer of a biocompatible polymer, at least one layer of a biocompatible superelastic/shape memory material, and at least one layer of a biocompatible adherent material. The deployment device includes a handle section and a deployment section, and the deployment section is configured to retain the patch for delivery of the patch to the tissue surface. The patch may include one or more arms, a base, and barbs extending from the arms, and advancing the deployment device to the tissue surface may include advancing the deployment device to the tissue surface of the heart for treatment of, for example, congestive heart failure.

20 Claims, 28 Drawing Sheets

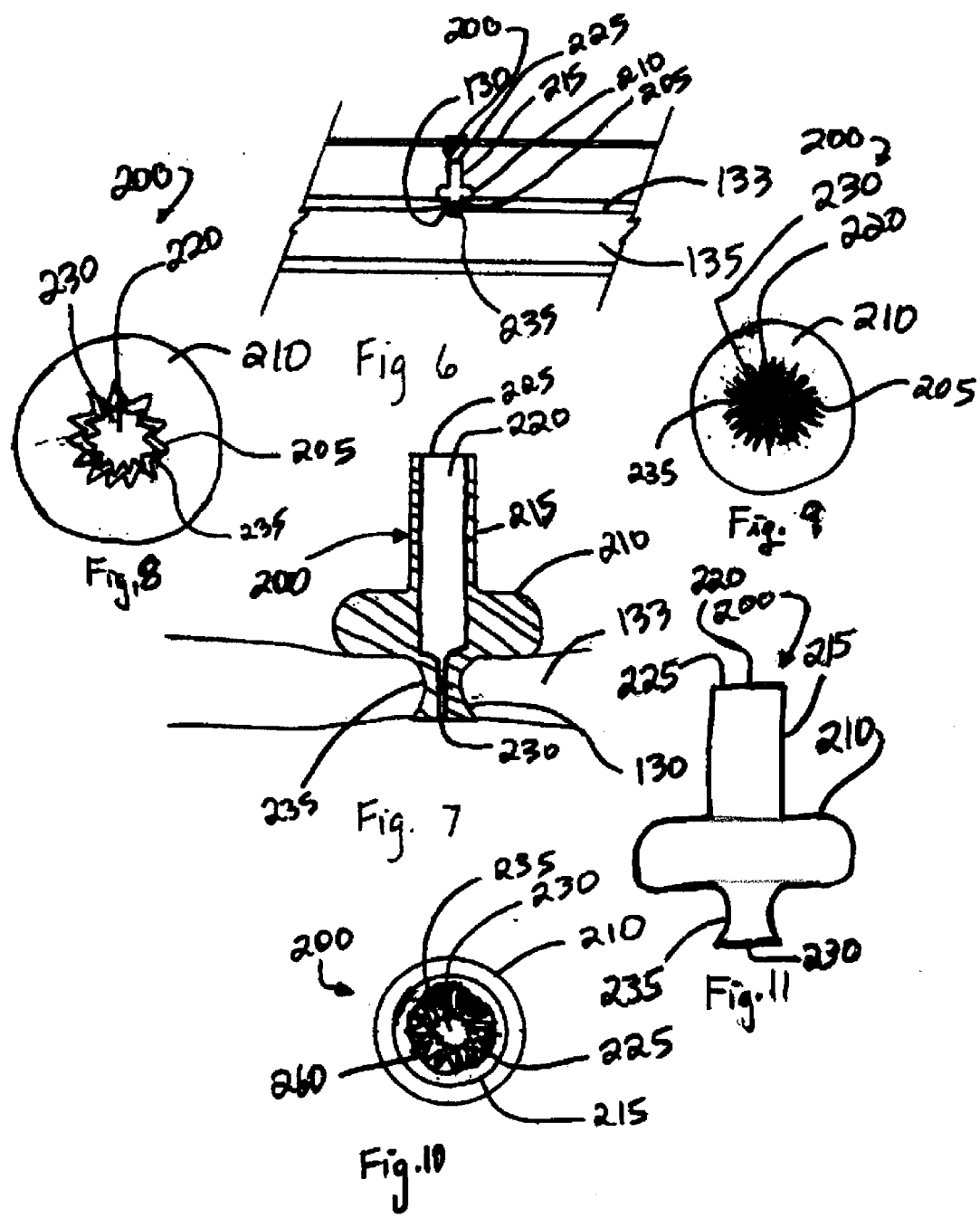

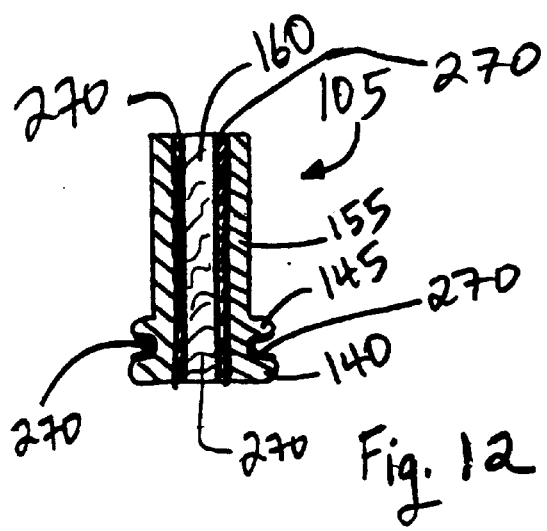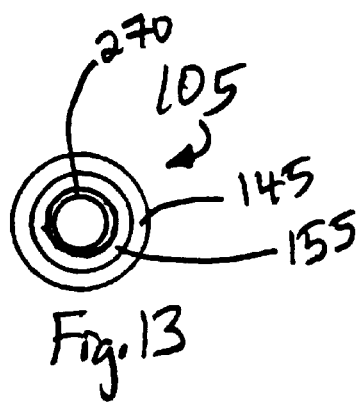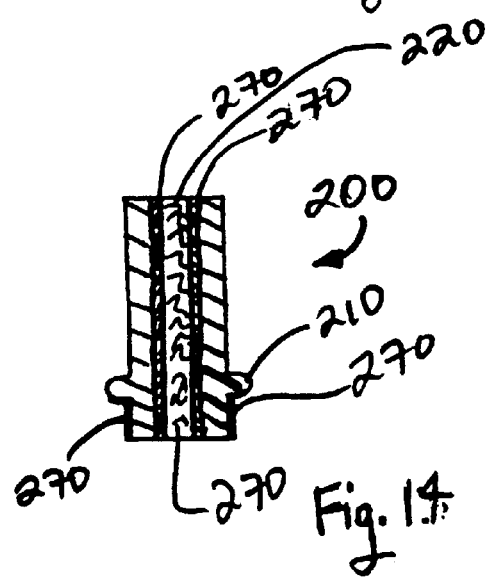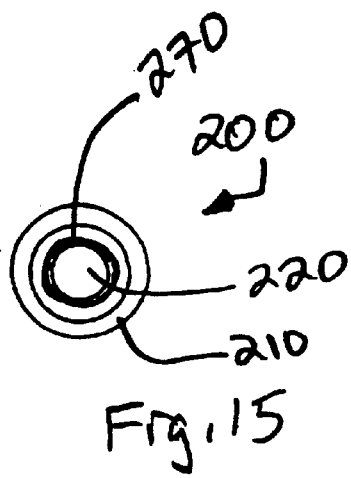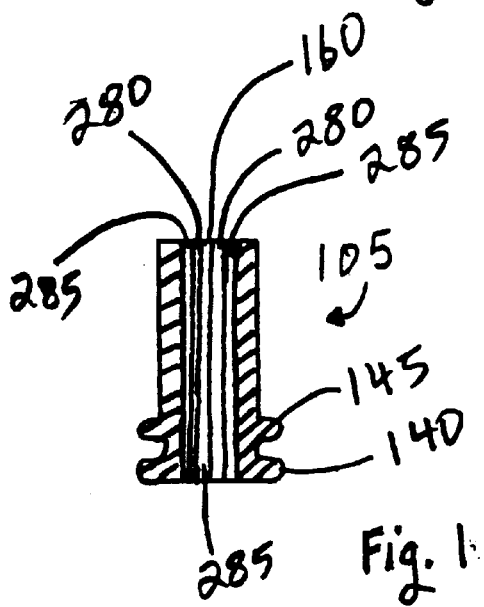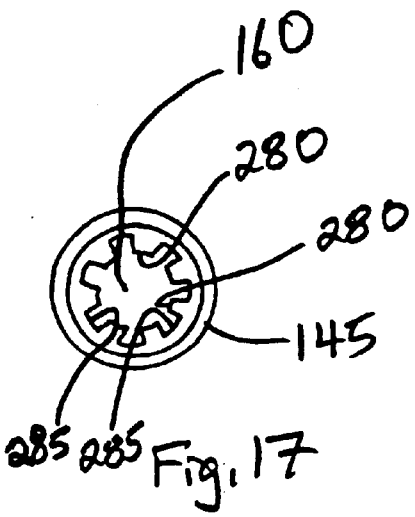

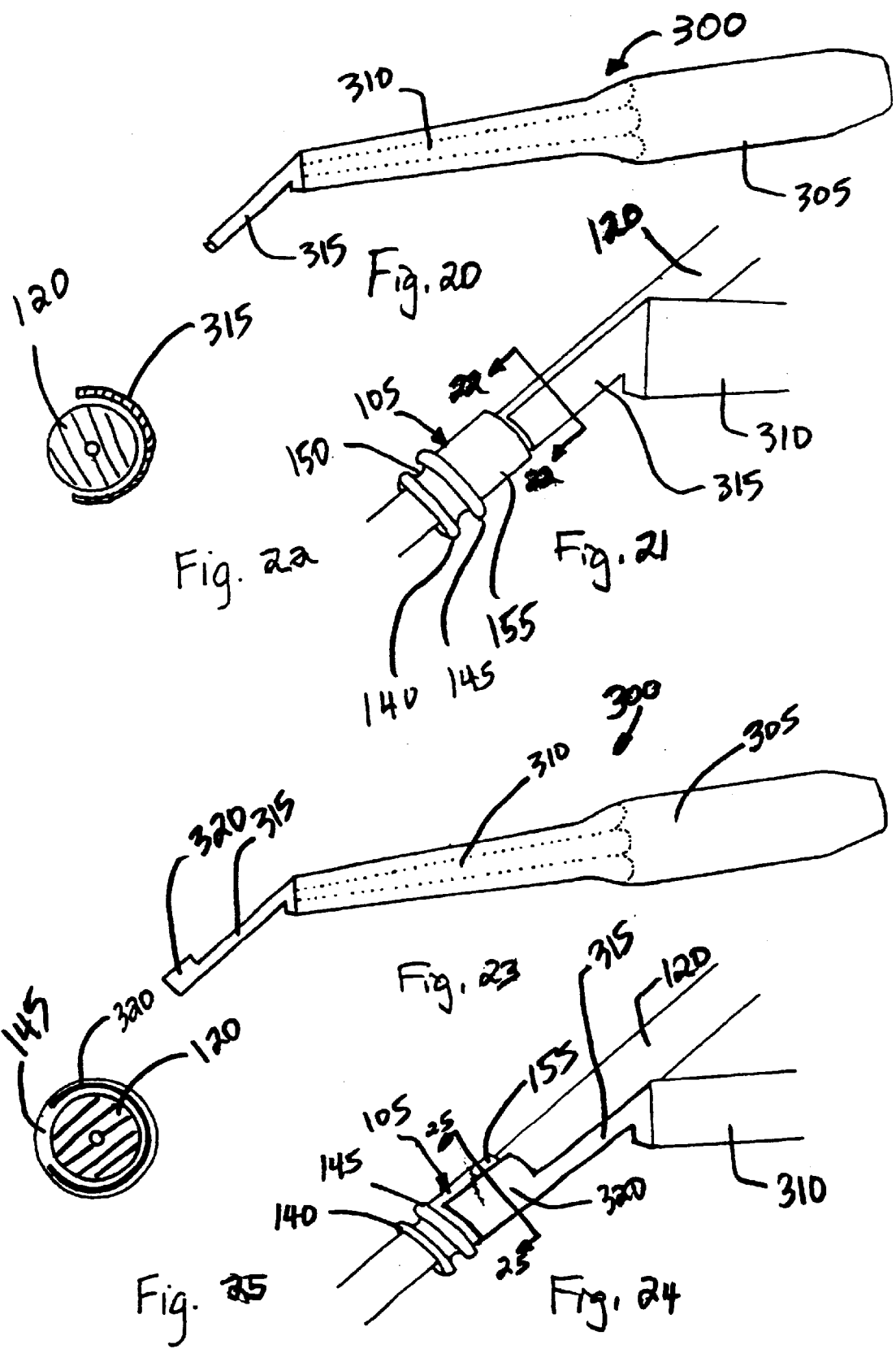

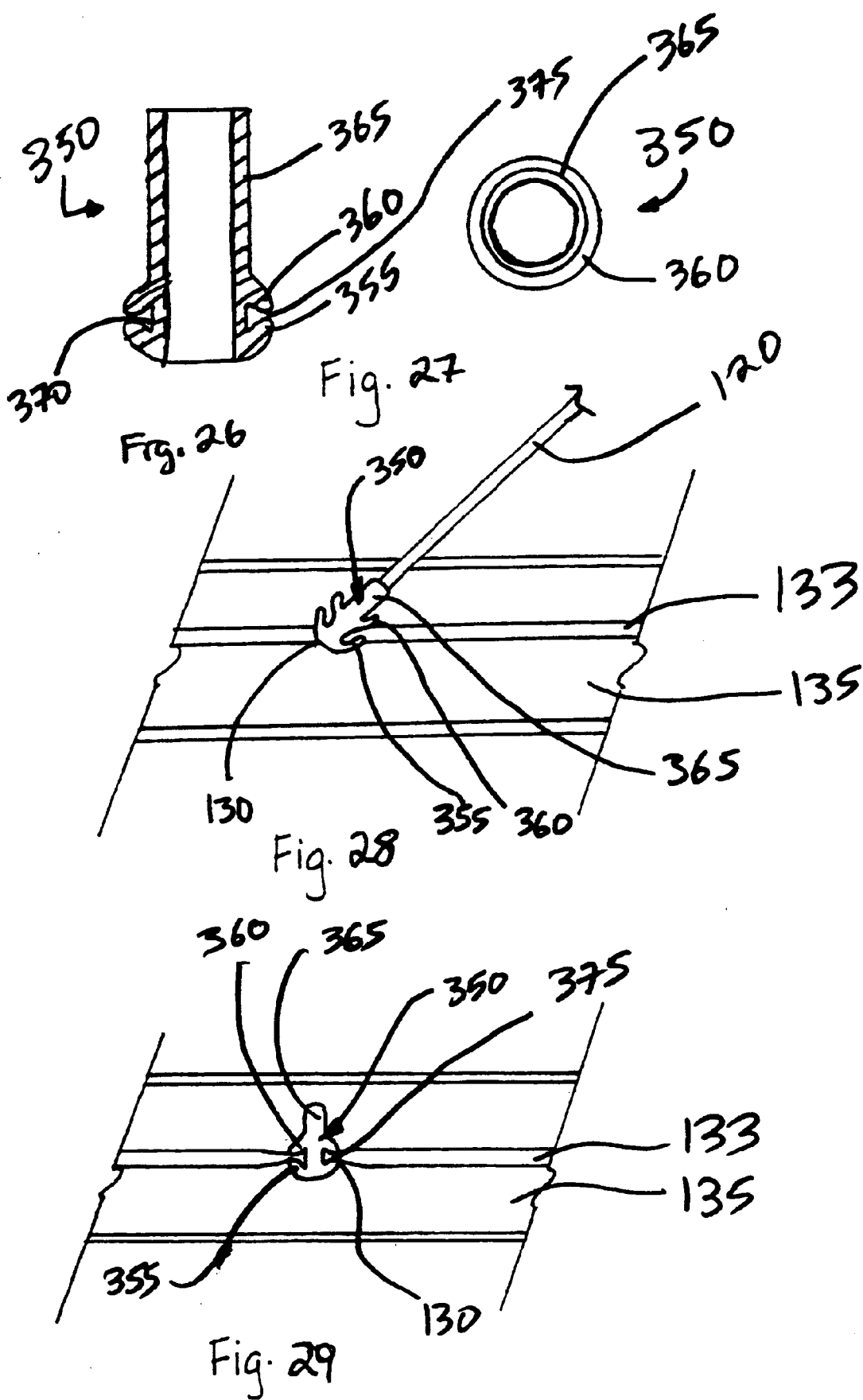

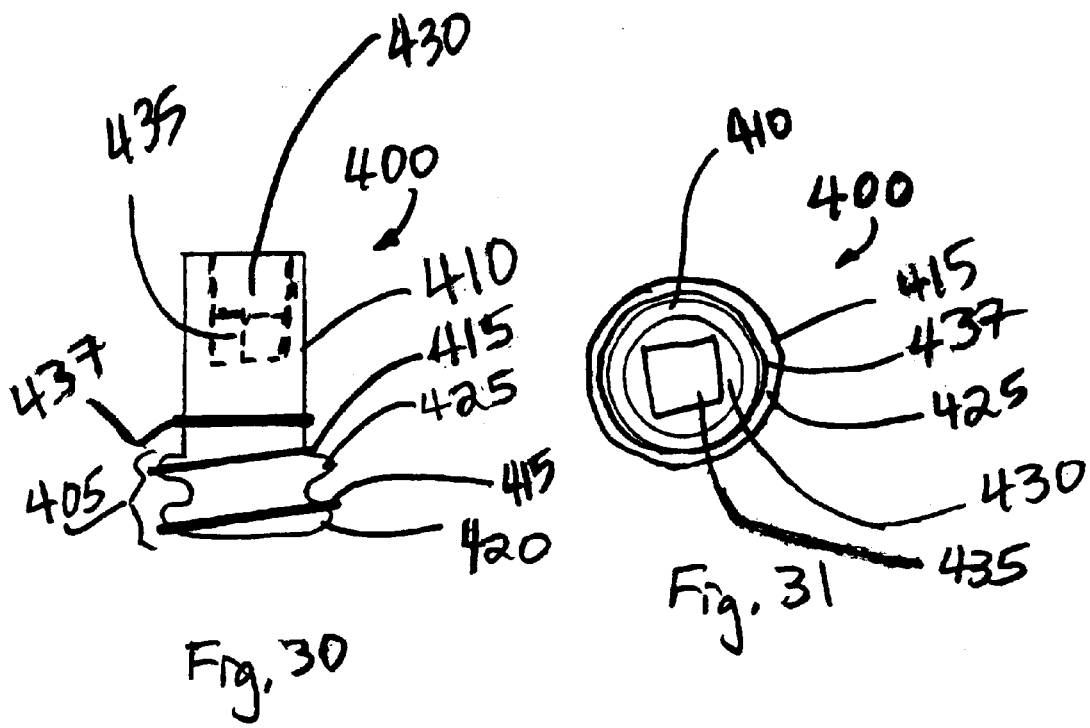
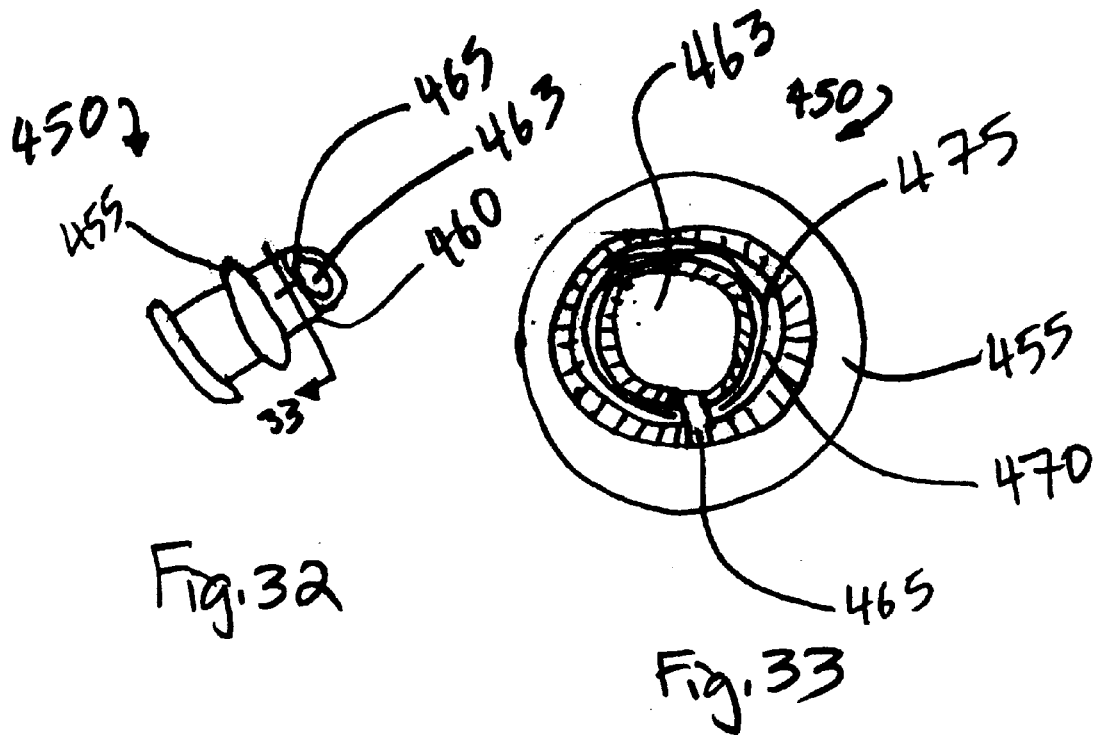

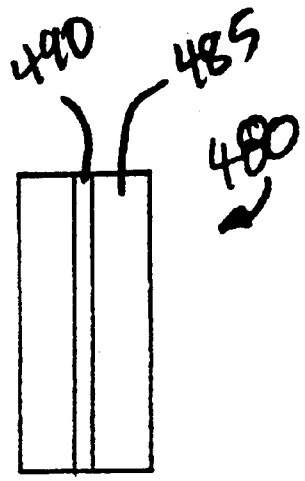
Fig. 34
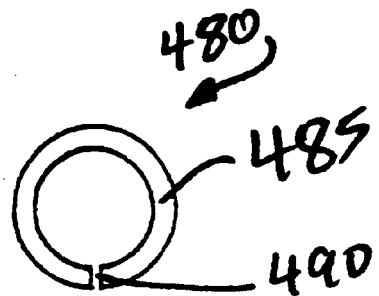
Fig. 35
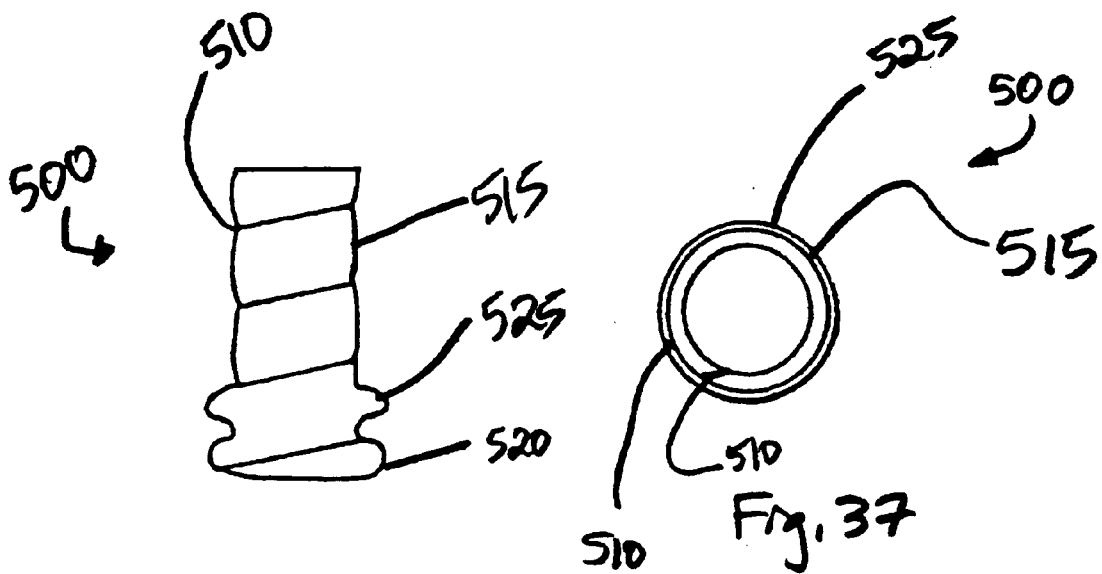
Fig. 36
Fig. 37

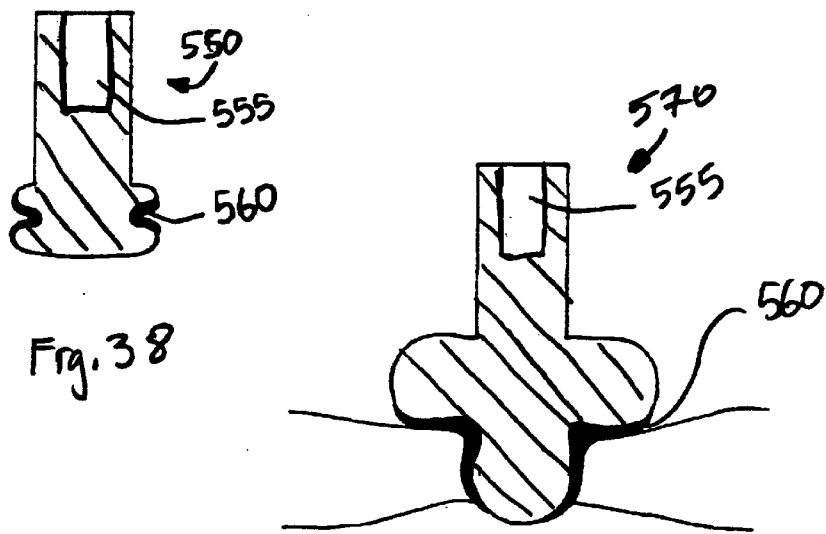
Fig. 38
Fig. 39
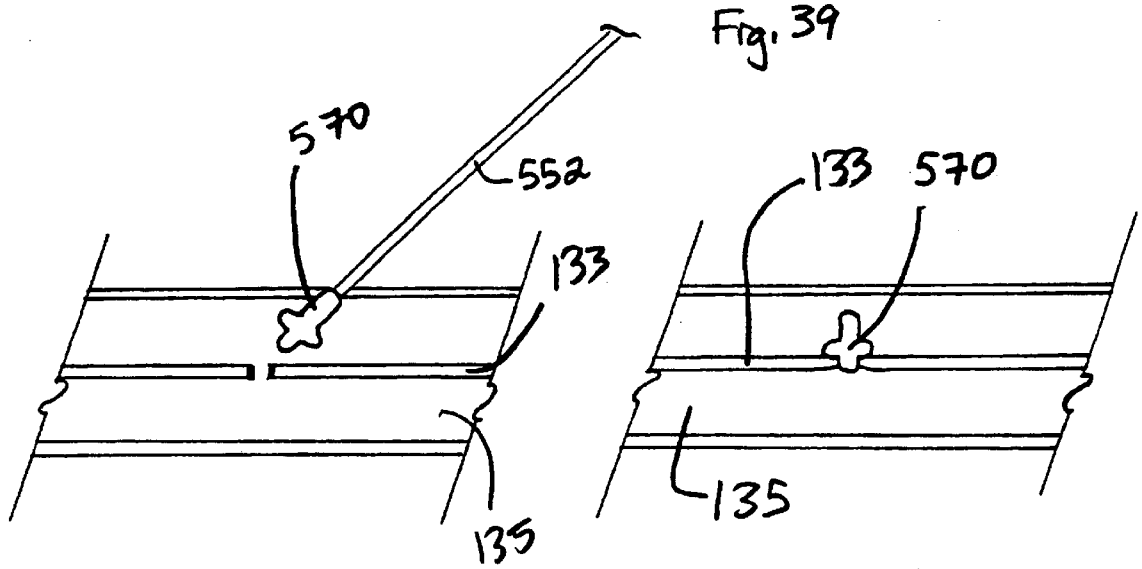
Fig. 40
Fig. 41

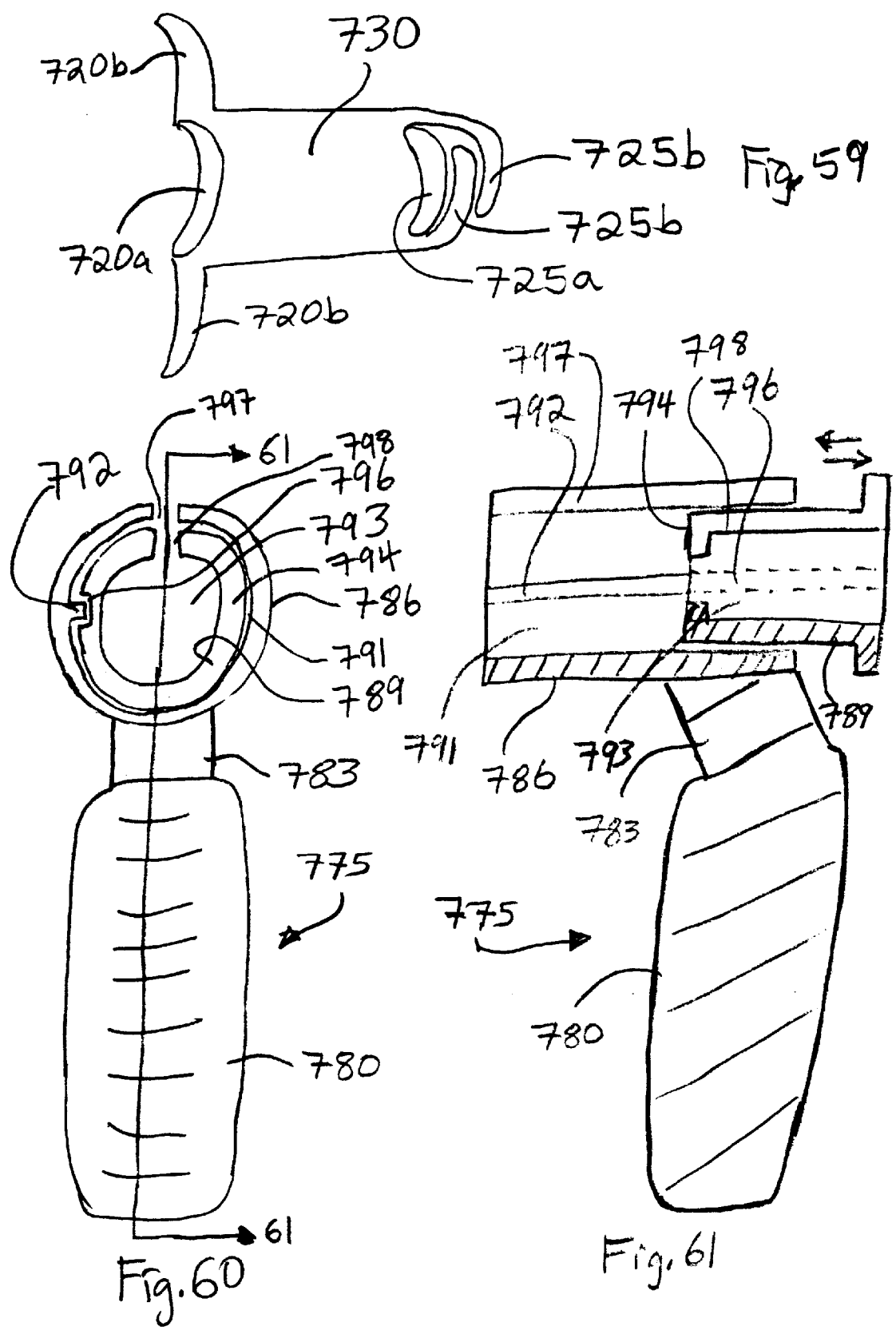

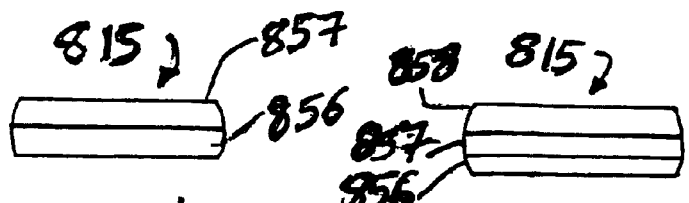
Fig. 64a  Fig. 64b  Fig. 64c
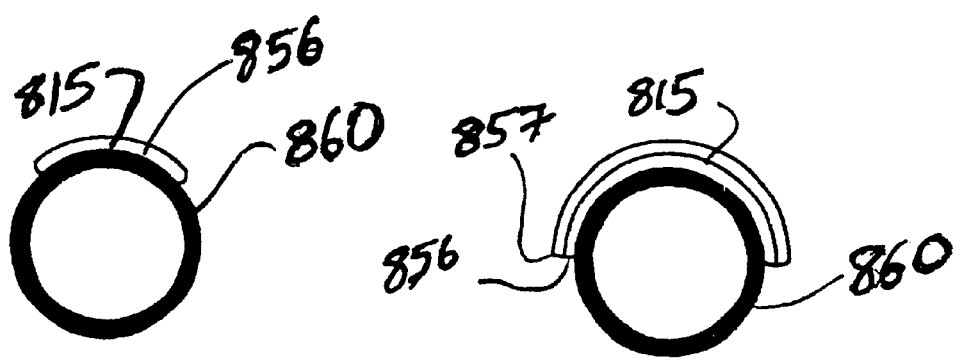
Fig. 65a  Fig. 65b
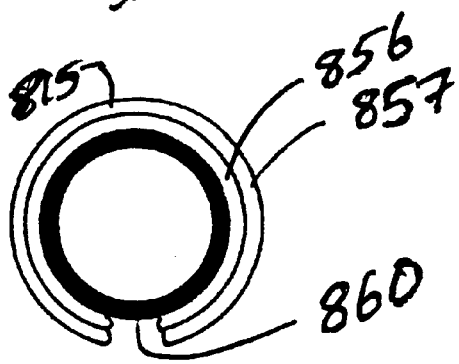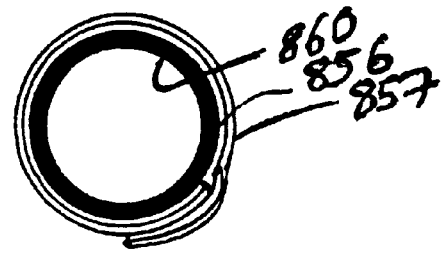
Fig. 65c  Fig. 65d

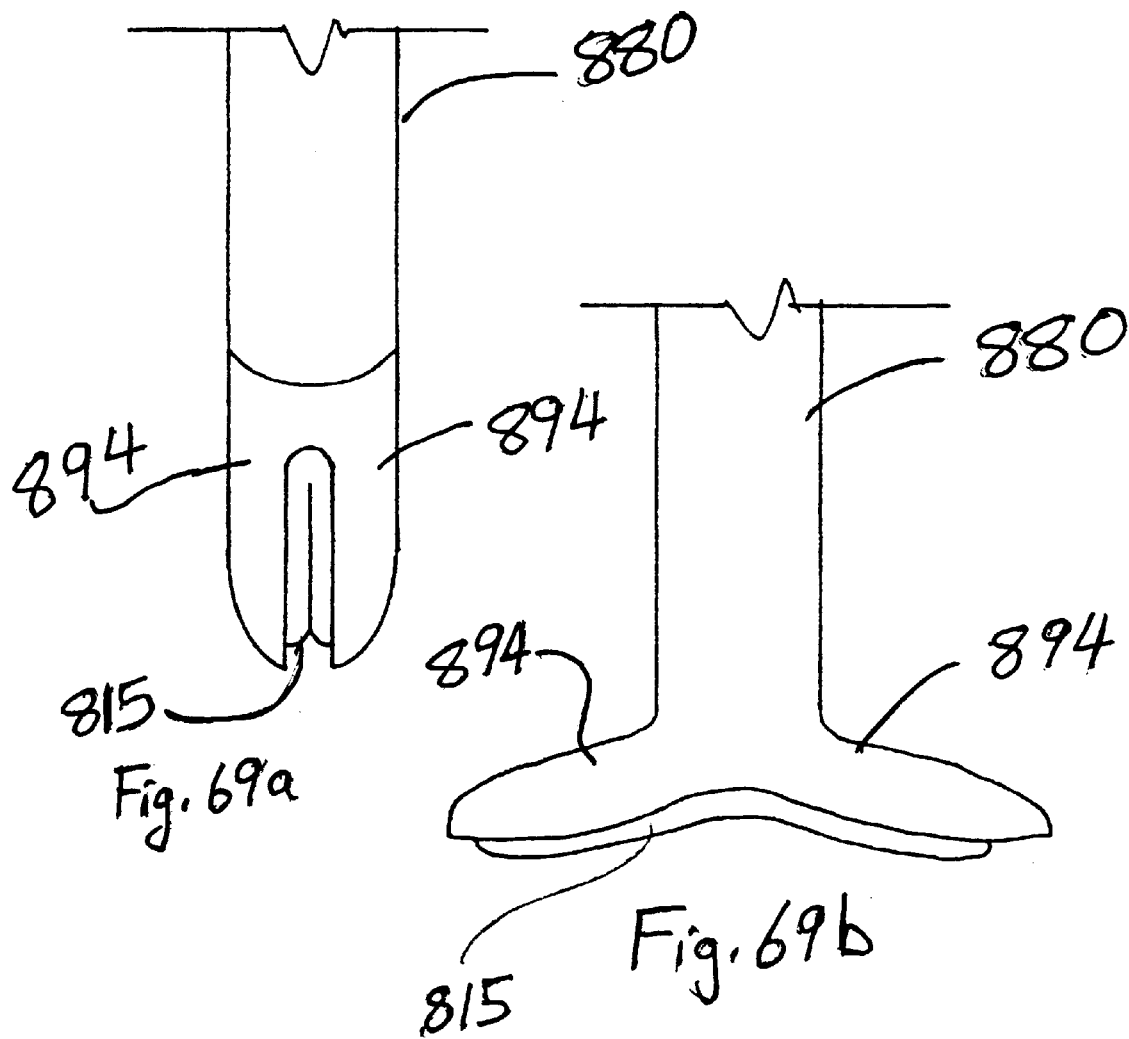

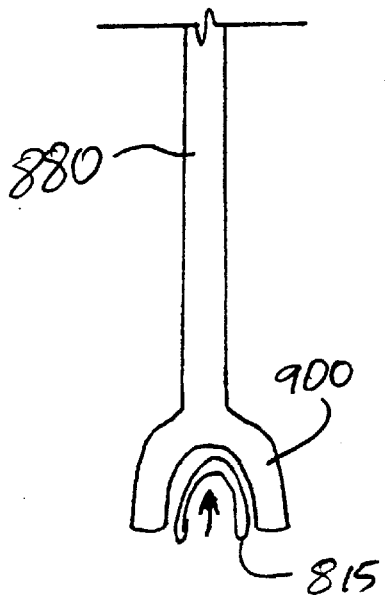
Fig. 70
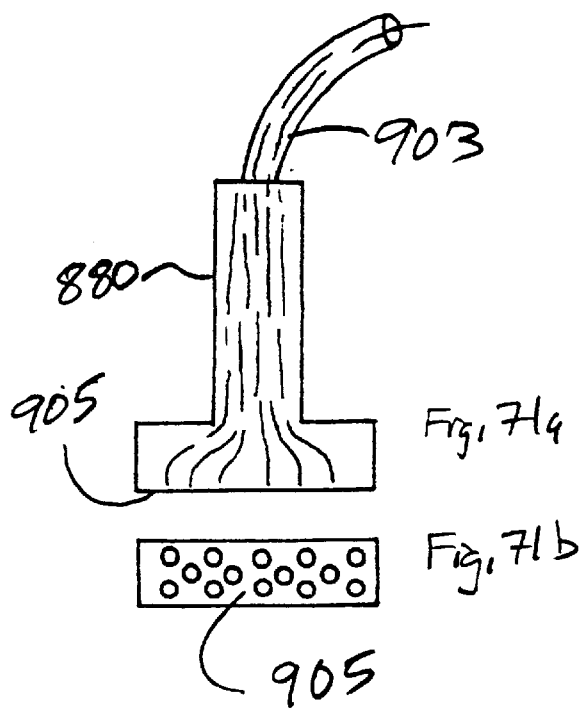
Fig. 71a
Fig. 71b
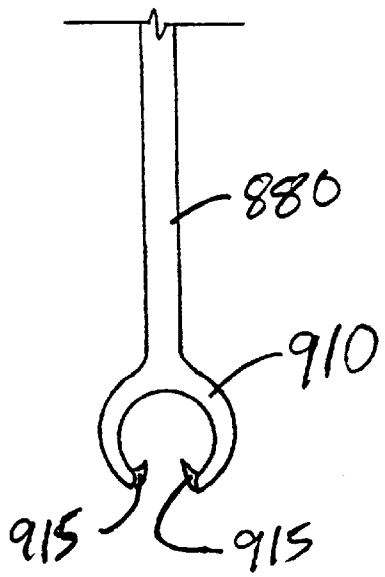
Fig. 72
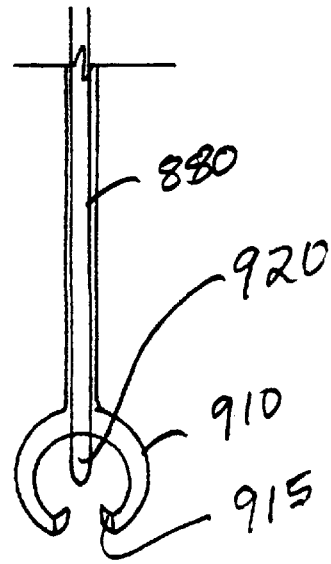
Fig. 73
Fig. 74
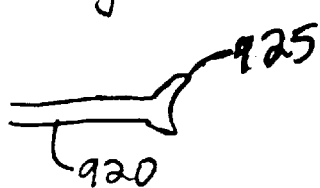

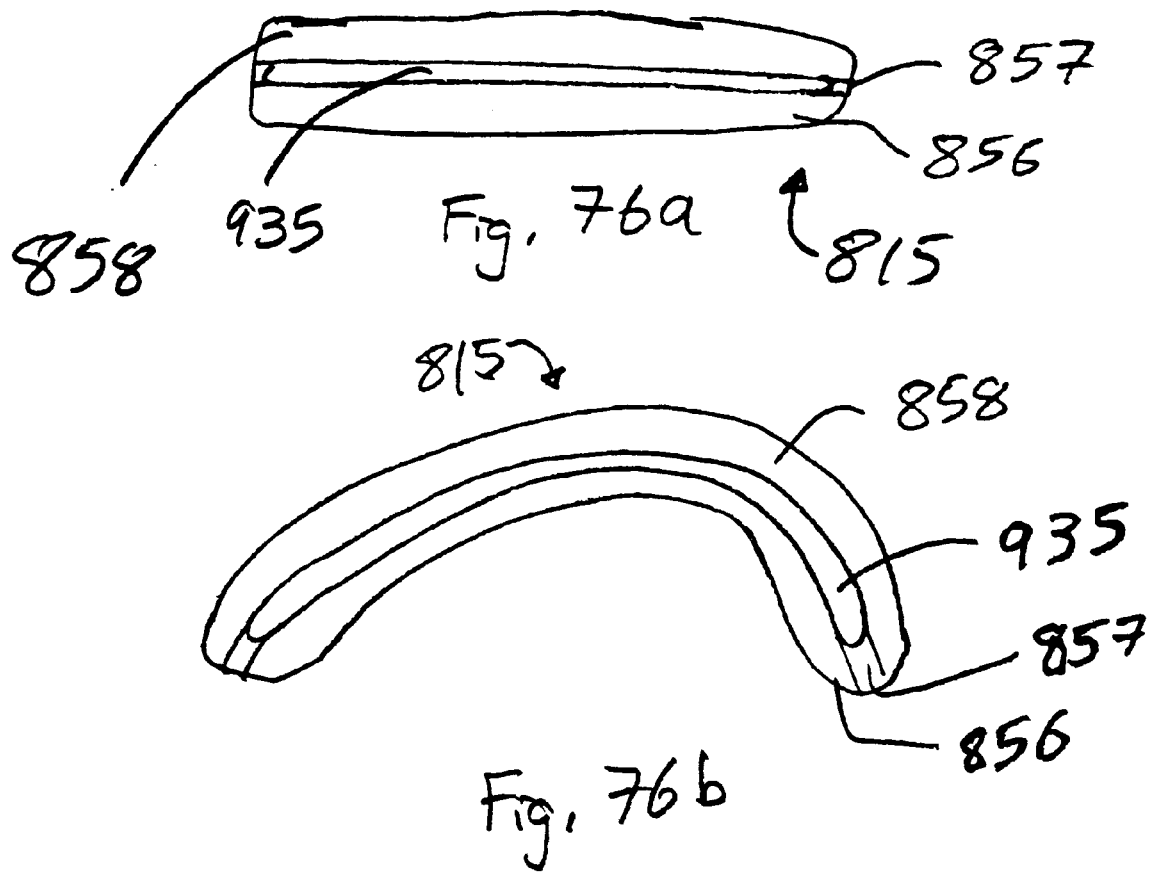

PATCHES AND COLLARS FOR MEDICAL APPLICATIONS AND METHODS OF USE

RELATED APPLICATIONS

This application claims priority from and is a continuation-in-part of U.S. patent application Ser. No. 10/127,714, filed on Apr. 23, 2002, which claims priority from U.S. Provisional Patent Application No. 60/286,269, filed Apr. 24, 2001 and titled Percutaneous Vessel Access Closure Device and Method; from U.S. Provisional Patent Application No. 60/300,892, filed Jun. 25, 2001 and titled Percutaneous Vessel Access Closure Device and Method, and from U.S. Provisional Patent Application No. 60/302, 255, filed Jun. 28, 2001 and titled Percutaneous Vessel Access Closure Device and Method (Hemostatic Patch or Collar), each of which is incorporated herein in their entirety by reference.

TECHNICAL FIELD

The field of the inventions generally relates to cardiovascular and closure devices, and, more particularly, to patches for placing against tissue.

BACKGROUND

In most cardiology and radiology procedures, a catheter is inserted into an artery, such as the femoral artery, through a vascular introducer. When the procedure is complete, the physician removes the catheter from the introducer and then removes the introducer from the arteriotomy into the vessel. The physician then must prevent or limit the amount of blood that leaks through the arteriotomy so that the patient can be discharged. Physicians currently use a number of methods to close the arteriotomy, such as localized compression, sutures, collagen plugs, and adhesives, gels, foams, and similar materials. To use localized compression, the physician presses down against the vessel to allow the arteriotomy to naturally clot. This method, however, can take half an hour or more, and requires the patient to remain immobilized for at least that period of time and be kept in the hospital for observation. There are potentials for clots at puncture site to be dislodged. Moreover, the amount of time necessary for the compression can be significantly increased depending upon how much heparin, glycoprotein IIb/IIA antagonists, or other anti-clotting agents were used during the procedure. Sutures and collagen plugs may have procedure variability, may require time to close the vessel, may have negative cost factors, and may necessitate a separate deployment device. Adhesives, gels, and foams may have negative cost factors, may necessitate a possibly complicated deployment process, and may have procedure variability.

SUMMARY

In one general aspect, a patch for placing against a tissue within a mammalian includes at least one layer of a biocompatible polymer, at least one layer of a biocompatible superelastic/shape memory material, and at least one layer of a biocompatible adherent material.

Embodiments of the patch may include one or more of the following features. For example, the superelastic/shape memory material may include a nickel titanium alloy. The alloy may include Nitinol. The superelastic/shape memory material may have a curved configuration in a resting state.

The patch may further include barbs extending from the superelastic/shape memory material. The patch may further include a power source connected to the patch and configured to provide power to the barbs.

The layer of superelastic/shape memory material is encapsulated by the polymer. The patch may be intended to close an opening in the vessel. The patch may include multiple arms and a base configured to form a concave shape. One or more barbs may extend from the arms.

The patch may further include a deployment device configured to deploy the patch. The deployment device includes a handle and a deployment section with the deployment section configured to retain the patch for delivery of the patch to the vessel. The deployment section may include a pair of openable jaws and/or a surface configured to apply a vacuum.

In another general aspect, applying a patch to a tissue surface within a mammalian body includes retaining the patch to a deployment device, advancing the deployment device to the tissue surface, pressing the patch against the tissue surface, and manipulating the deployment device to separate the deployment device from the patch and leave the patch against the tissue surface. The patch includes at least one layer of a biocompatible polymer, at least one layer of a biocompatible superelastic/shape memory material, and at least one layer of a biocompatible adherent material. The deployment device includes a handle section and a deployment section, and the deployment section is configured to retain the patch for delivery of the patch to the tissue surface.

Embodiments may include one or more of the following features. For example, retaining the patch to the deployment device may include using an adhesive to retain the patch to the deployment device. Retaining the patch to the deployment device may include applying vacuum to the patch. Manipulating the deployment device to separate the deployment device from the patch may include moving the deployment device relative to the tissue surface to which the patch is applied. Manipulating the deployment device to separate the deployment device from the patch may include advancing a plunger within the deployment device. Manipulating the deployment device to separate the deployment device from the patch may include opening a pair of jaws in the deployment section.

The patch may include one or more arms, a base, and barbs extending from the arms, and advancing the deployment device to the tissue surface may include advancing the deployment device to the tissue surface of the heart.

The details of various embodiments of the invention are set forth in the accompanying drawings and the description below. Other features and advantages of the invention will be apparent from the description, the drawings, and the claims.

DESCRIPTION OF THE DRAWINGS

FIGS. 6 and 7 are side and cross-sectional side views, respectively, of a second implementation of a arterial closure device deployed within an arteriotomy of a vessel wall.

FIG. 8 is a bottom end view of the arterial closure device of FIG. 6 showing the flared end opened.

FIG. 9 is a bottom end view of the arterial closure device of FIG. 6 showing the flared end closed.

FIG. 10 is a top end view of the arterial closure device of FIG. 6 showing the flared end partially closed.

FIG. 11 is a side view of the arterial closure device of FIG. 6 showing the flared end.

FIGS. 12 and 13 are a cross-sectional side view and a top view, respectively, of the arterial closure device of FIG. 1 having an adhesive on the inner diameter and tissue engagement areas.

FIGS. 14 and 15 are a cross-sectional side view and a top view, respectively, of the arterial closure device of FIG. 6 having an adhesive on the inner diameter and tissue engagement areas.

FIGS. 16 and 17 are a cross-sectional side view and a top view, respectively, of the arterial closure device of FIG. 1 having grooves on the inner diameter to form a thinned or weakened wall.

FIG. 20 is a side view of a deployment tool.

FIG. 21 is a side view of the deployment tool of FIG. 20 used to deploy a arterial closure device.

FIG. 22 is an end view of the deployment tool FIG. 20.

FIG. 23 is a side view of the deployment tool of FIG. 20 having an extended contacting member.

FIG. 24 is a side view of the deployment tool of FIG. 23 used to deploy a arterial closure device.

FIG. 25 is an end view of the deployment tool FIG. 23

FIG. 26 is a cross-sectional side view of a arterial closure device having angled closure edges for compressing a vessel wall.

FIG. 27 is a top view of the arterial closure device of FIG. 26.

FIG. 28 is a side view of the arterial closure device of FIG. 26 being advanced through the skin into a vessel with the closure edges deflected.

FIG. 29 is a side view of the arterial closure device of FIG. 26 deployed and secured onto vessel wall with the closure edges occluding the arteriotomy.

FIG. 30 is a side view of a arterial closure device.

FIG. 31 is an end view of the arterial closure device of FIG. 30.

FIG. 32 is a perspective side view of a vascular connector having a closable end.

FIG. 33 is an end view of the arterial closure device of FIG. 32.

FIG. 34 is a side view of a liner having a longitudinal slot for a arterial closure device.

FIG. 35 is an end view of the liner of FIG. 34.

FIG. 36 is a side view of a liner having a radial slot.

FIG. 37 is an end view of the liner of FIG. 36.

FIG. 38 is a side view of a plug-style arterial closure device that includes an adhesive layer on the vessel contact areas.

FIG. 39 is a side view of a plug style arterial closure device that has limited vessel protrusion and includes an adhesive on the vessel contacting areas.

FIGS. 40 and 41 are side views of the plug style arterial closure device of FIG. 39 being deployed and deployed within a vessel.

FIG. 59 is a side view of a configuration having side arms that fold over each other.

FIGS. 60 and 61 are front and cross-sectional side views of a deployment tool for deploying the arterial closure device.

FIGS. 64a–c are side views of the patches/collars of FIGS. 63a–j.

FIGS. 65a–d are side views of the patches/collars of FIGS. 64a–c applied to a tubular vessel.

FIGS. 69a and b are side views of a patch/collar mounted in the jaws of the deployment device of FIG. 68a.

FIG. 70 is a side view of the deployment device having a semi-circular end.

FIGS. 71a and 71b are side and bottom views, respectively, of a vacuum assisted deployment device.

FIG. 72 is a side view of the deployment device having a semi-circular end with retaining prongs.

FIG. 73 is a side view of the deployment device having a plunger to deploy the patch/collar.

FIG. 74 is a side view of a second embodiment of the plunger of FIG. 73.

FIGS. 76a and 76b are side views of a patch/collar that includes a superelastic or shape memory element.

DETAILED DESCRIPTION

Figure 1:
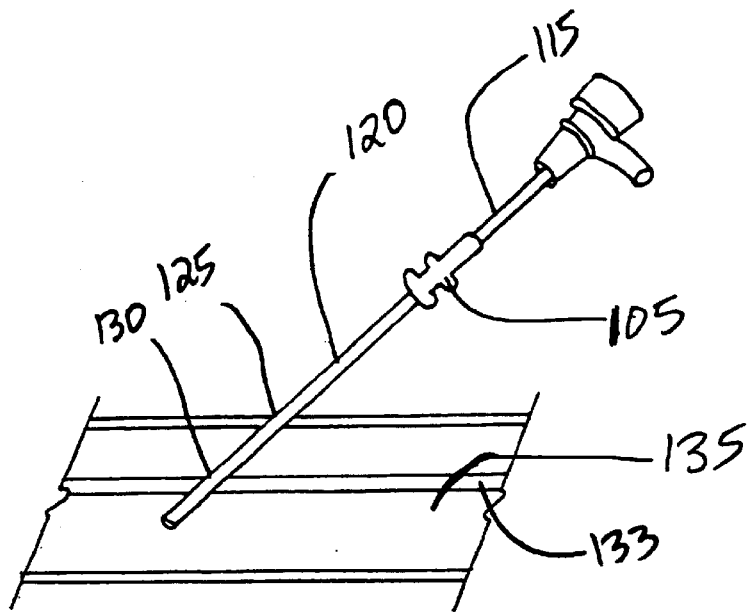
FIG. 1 is a side view of a arterial closure device positioned around a tubular section of a vascular introducer.
Figure 2:
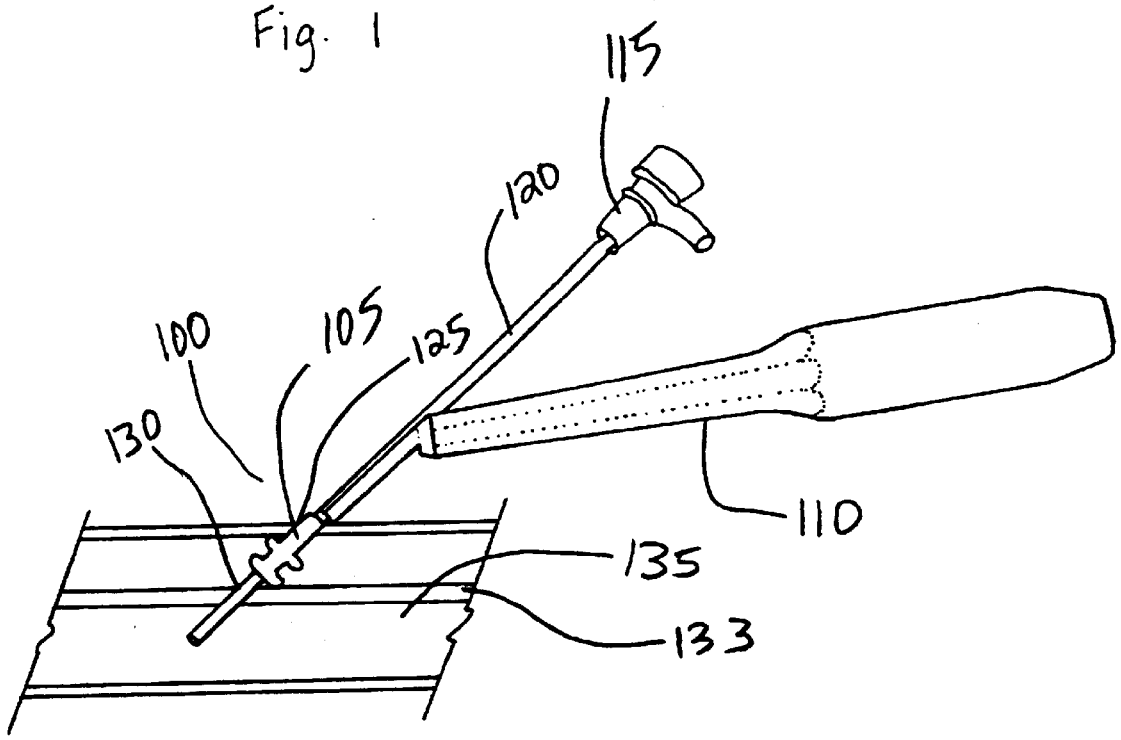
FIG. 2 is a side view of the arterial closure device of FIG. 1 advanced through a percutaneous opening by a deployment instrument.
Figure 3:
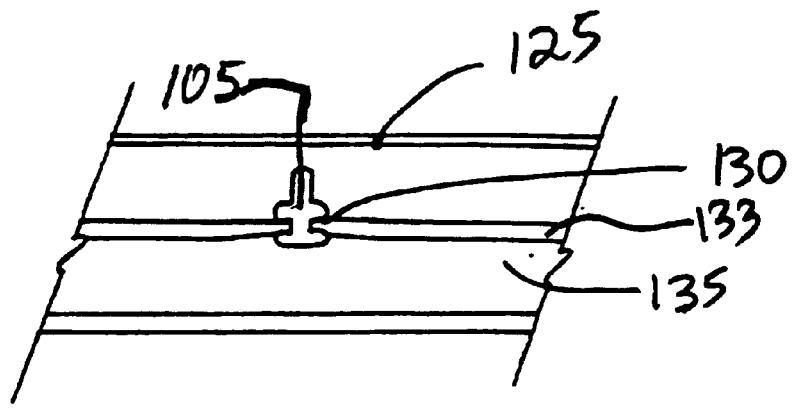
FIG. 3 is a side view of the arterial closure device of FIG. 1 deployed through a vessel wall.

Referring to FIGS. 1–3, a vascular closure system 100 generally includes two components: a arterial closure device ("ACD") 105 and a deployment instrument 110. The ACD 105 is slidably mounted to a vascular introducer 115 or other tubular device, such as a catheter, advanced over a tube section 120 of the introducer 115 using the deployment instrument 110, passed through a percutaneous opening 125, and placed through an arteriotomy 130 in a vessel wall 133 into a blood vessel 135. The deployment tool 110 and the introducer 115 then are removed from the blood vessel 135 and out of the percutaneous opening 125.

Figure 4:
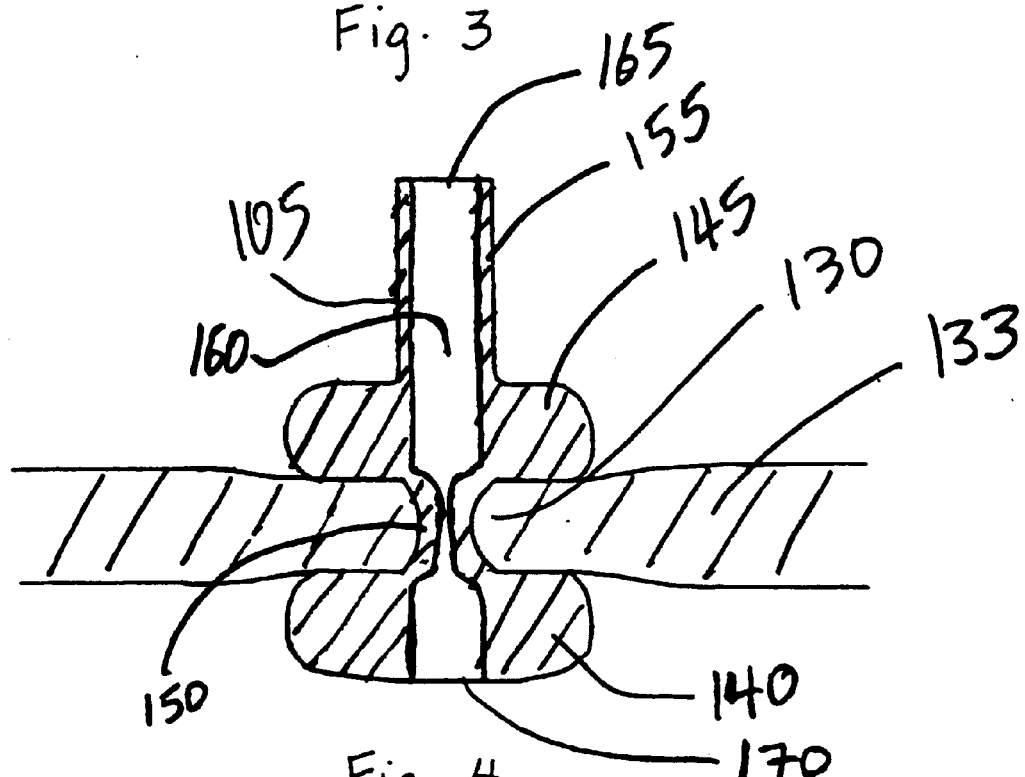
FIG. 4 is a cross-sectional side view of the arterial closure device of FIG. 1 deployed through a vessel wall.
Figure 5:
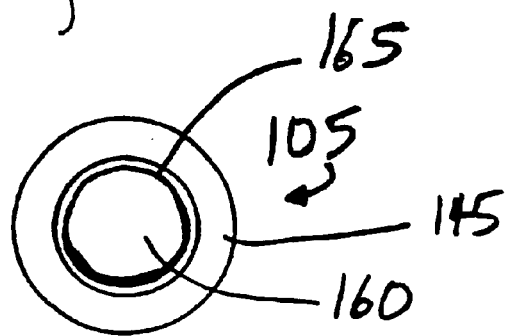
FIG. 5 is a top view of the arterial closure device of FIG. 1.

Referring to FIGS. 4 and 5, the ACD 105 is generally compliant, tubular, and includes a first member 140, a second member 145, a connecting member 150 between the first member and the second member, and an optional extending member 155 that extends from the second member. A longitudinal channel 160 passes between a first opening 165 in the extending member (or second member if the extending member is not present) and a second opening 170 in the first member 140.

The ACD 105 is formed of a tubular structure of sufficient length and thickness (e.g., a single wall thickness of between 0.005" and 0.05", and more particularly between 0.01" and 0.02") that can be advanced over the introducer 115, and through the puncture site 125. The ACD 105 has sufficient rigidity to be advanced through the puncture site 125 yet is compliant enough to be compressed onto itself by the natural elasticity of the vessel wall 133 after the introducer 115 is removed. Moreover, the connecting member 150 can be configured to have a natural elasticity such that when it is no longer mounted over the introducer tube 120, it will return to its original smaller diameter state. The ACD 105 may include, for example, longitudinal sections of the tube where the wall thickness is thinner (e.g., connecting member 150) thereby creating creases or weakened areas that receive the vessel wall 133. The creases would reduce the amount of compressive force required to collapse the tube onto itself. A design allowing tactile feedback may be used to determine the proper insertion position (depth). The tactile feedback could be accomplished by the ACD 105 having one or more rings of increased wall thickness, an "hour glass" geometry, a thin, narrow, then wide geometry, combination, or other means to provide an abrupt change in the advancing force resistance during deployment. The ACD 105 may be manufactured in many different French sizes, to match the outer diameter of any commercial vascular introducers 115.

The ACD 105 is placed around the outside of any commercially available introducer 115, or other device that is inserted into the cardiovascular system (e.g., catheter, etc.), and positioned adjacent to the proximal end of the introducer (i.e., near the valve or luer fitting of the introducer). The introducer 115 then is inserted into the vasculature using standard techniques. Prior to removing the introducer 115, the tubular ACD 115 is advanced to the skin, for example, by the physician manually advancing the ACD along the tube 120. The deployment instrument 110 then is positioned against or clipped onto the tuber 120, advanced to be in contact with the proximal end (i.e., second member 145) of the ACD 105, and advanced through the skin such that at least the distal most portion (e.g., first member 140) of the ACD is inside the vessel 135. The ACD 105 is prevented from deforming or collapsing during insertion by the rigidity of the tube 120. The tube 120 also acts as a guide to position the ACD 105 through the puncture site 125 during its advancement and deployment. When the introducer 115 is removed, the deployment instrument 110 is held in position and still in contact with the ACD 105 preventing the ACD from coming out of the vessel 135 along with the introducer. Once the introducer 115 is completely removed, the ACD 105 is compressed together due to the elastic recovery of the vessel wall 133, achieving hemostasis and effectively sealing the arteriotomy 150 and puncture site 125.

The ACD 105 can be partially or completely fabricated from a biocompatible material, such as expanded polytetrafluoroethylene (ePTFE), polyester, polyurethane, silicone, Dacron, urethane, and/or a composite or combination of these or other suitable materials. The ACD 105 also can be partially or completely fabricated from a biodegradable/bioabsorbable material, including modified cellulose, collagen, fibrin, fibrinogen, elastin or other connective proteins or natural materials, polymers or copolymers such as polylactide [poly-L-lactide (PLLA), poly-D-lactide (PDLA)], polyglycolide, polydioxanone, polycaprolactone, polygluconate, polylactic acid (PLA), polylactic acid-polyethylene oxide copolymers, poly(hydroxybutyrate), polyanhydride, polyphosphoester, poly(amino acids), poly(alpha-hydroxy acid) or related copolymers of these materials as well as composites and combinations thereof and combinations of other biodegradable/bioabsorbable materials.

The ACD 105 also can be partially or completely fabricated from materials that swell, or expand when they are exposed to a fluid, such as blood, or another fluid, for example, that can be added by the physician to cause the material to swell. These materials include hydrophilic gels (hydrogels), regenerated cellulose, polyethylene vinyl acetate (PEVA), as well as composites and combinations thereof and combinations of other biocompatible swellable or expandable materials.

The ACD 105 can be made using several methods and processes including extrusion, molding (i.e., injection molding or other known molding techniques), casting, dip coating, spraying, adhesive bonding, ultra-sonic welding, composite fabrication techniques, and combinations of these and/or other similar methods and processes.

The ACD 105 also can have a biocompatible contact adhesive or other material within the longitudinal channel 160 so that when the longitudinal channel is compressed within the arteriotomy 130, the adhesive bonds the inside surfaces of the longitudinal channel together. This assists or expedites the sealing of the arteriotomy. Additionally, bonding materials can be used on the outside of the ACD 105, for example, on the outer surface of the first member 140, the second member 145, the connecting member 150, and or the optional extending member 155. In particular, the bonding material is especially useful where the ACD contacts the vessel wall 133 defining the arteriotomy 130.

The biocompatible contact adhesive adhesive/bonding compounds/solutions could be added during the manufacturing process, just prior to deployment, or after the device has been deployed. The bonding materials could be in the form of a liquid, semi solid, or solid. Suitable bonding materials include gels, foams and microporous mesh. Suitable adhesives include acrylates, cyanoacrylates, epoxies, fibrin-based adhesives, other biological based adhesives, UV light and/or heat activated or other specialized adhesives. The adhesive could bond on initial contact, or longer, to allow repositioning if desired. The preferred adhesive may be a crystalline polymer that changes from a non-tacky crystalline state to an adhesive gel state when the temperature is raised from room temperature to body temperature.

Such material is available under the trade name Intillemer™ adhesive, available from Landec Corp. as well as composites and combinations thereof and combinations of other materials. Suppliers of biocompatible adhesives include, but are not limited to, Plasto (Dijon, France), Haemacure (Montreal, Canada), Cohesion (Palo Alto, Calif.), Cryolife (Kennesaw, Ga.), TissueLink (Dover, N.H.), and others. To increase the work time of the adhesive or allow repositioning of the vascular coupler after it has been deployed, the adhesive can be blended with a material, such as a starch or other material, that retards or delays bonding to allow repositioning of the coupler after it has been deployed. A degradable coating can be placed over the adhesive coating so that it degrades and exposes the adhesive. Other adhesives are understood to include composites-based adherents and combinations of the above materials and other suitable materials as are known in the art.

To improve later detection of the ACD 105, it can be fabricated from materials that include one or more radiopaque materials, such as barium sulfate, bismuth trioxide, or other any other radiopaque material. The radiopaque material is added to the materials from which the ACD 105 is fabricated or to the bonding materials that are placed in, on, or around the ACD.

Referring to FIGS. 6–11, a second implementation of a arterial closure device is shown as a arterial closure device ("ACD") 200. The ACD 200 includes a first member 205, a second member 210, and an optional extending member 215 that extends from the second member. A longitudinal channel 220 passes between a first opening 225 in the extending member (or second member if the extending member is not present) and a second opening 230 in the first member 205. The ACD 200 is implanted within an arteriotomy 130 in a manner similar to the implantation of the ACD 105. However, the ACD 200 does not include a member that is substantially in contact with the inner wall of the vessel 135. Instead, the ACD has a flare, or two or more short slits 235 in the side wall of the first member 205. The flare or slits 235 are designed to open or flare around the catheter or introducer 120 when advanced to the top of the vessel puncture site (FIG. 8). The materials from which the ACD 200 or the second member 205 are fabricated may be a very elastic material such that when around the introducer it expands and when advanced beyond the end of the introducer, it contracts such that the individual flares pinch or otherwise catch the edges of the arteriotomy or punctured vessel and pull them together while contracting (FIG. 9). This action is intended to close the arteriotomy 130 and create hemostasis. The inside of the flared section 235 of the ACD 200 may have a biocompatible contact adhesive or other bonding material, as described above, that further secures the ACD within the arteriotomy and to the vessel 135, and, in particular the second member 210 to the top or outer surface of the vessel.

As indicated above, the adhesive or bonding materials can be implemented on any of the above ACDs. For example, referring to FIGS. 12 and 13, the ACD 105 has an adhesive or bonding material 270 on the inner diameter and tissue engagement areas. Similarly, referring to FIGS. 14 and 15, the ACD 200 has the adhesive or bonding material 270 on the inner diameter and tissue engagement areas. In this manner, adhesive 270 will close the respective longitudinal channel 160, 200 of the ACD 105, 200 to reduce or eliminate seepage blood. Moreover, the adhesive 270 around the tissue contacting areas will bond the ACD to the vessel wall to reduce or eliminate seepage of blood through those regions.

Referring to FIGS. 16 and 17, the ACD 105 can have the inner diameter of the longitudinal channel 160 modified to include ridges 280 and channels 285 that weaken or thin the wall section of the ACD. In this manner, the inner diameter of the longitudinal channel 160 can be expanded or reduced depending upon the circumferential pressure exerted against the ACD. For example, when passing the introducer through the longitudinal channel the inner diameter will be expanded. When the introducer is subsequently removed, the inner diameter is reduced because of the natural elastic recoil properties of the ACD. In this manner, the seepage of blood through the longitudinal channel is reduced or eliminated. Moreover, the surfaces of the inner diameter of the longitudinal channel can be coated with an adhesive, as described above, to further ensure that the inner diameter is closed.

The ACDs described herein also can include one or more therapeutic agents that affect healing at the site where the device is deployed. The agent(s) can be incorporated into the structure forming the device and/or incorporated into a coating. Such therapeutic agents may include, but are not limited to, antithrombotics (such as anticoagulants), antimitogens, antimitotoxins, antisense oligonucleotides, gene therapy solutions, nitric oxide, and growth factors and inhibitors. Direct thrombin inhibitors that may be beneficial include Hirudin, Hirugen, Hirulog, PPACK (D-phenylalanyl-L-propyl-L-arginine chloromethyl ketone), Argatreban, and D-FPRCH.sub.2 Cl (D-phenylalanyl-L-propyl-L-arginyl chloromethyl ketone); indirect thrombin inhibitors include Heparin and Warfarin (coumadin). Alternatively, a clot promoter may be used, such as protamine sulphate or calcium hydroxide. Additional therapeutic materials include, aspirin, dexamethasone, dexamethasone phosphate, streptokinase, tocopherol, TPA, urokinase, paclitaxel (Taxol), actinomycin, rapamyacin, or other. Sirolimus, or other antibiotics may also be used. The therapeutic compounds/solutions may be blended with the device base materials during fabrication, applied just prior to deployment, or after the device has been deployed. Additionally, the therapeutic materials may be located on, through, inside, or combination of the device in holes, grooves, slots or other indentation to allow elution of the therapeutic compound(s). Post device fabrication coating methods include, but are not limited to, dipping, spraying, brushing, submerging the devices into a beaker containing a therapeutic solution while inside a vacuum chamber to permeate the device material, etc.

Figure 18:
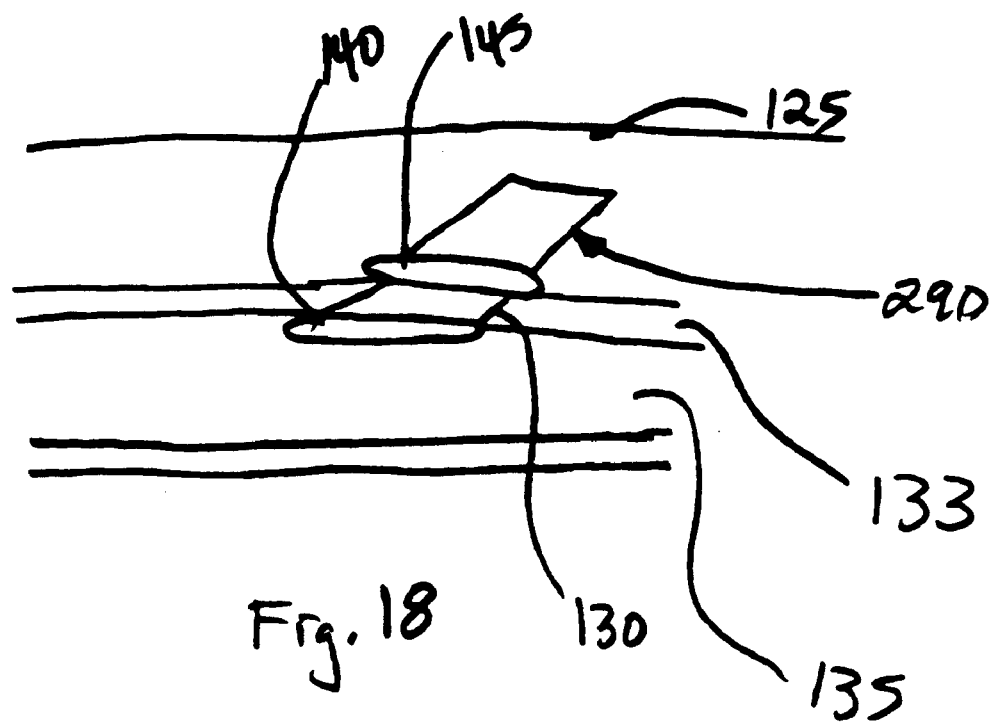
FIG. 18 is a side view of an angled arterial closure device.
Figure 19:
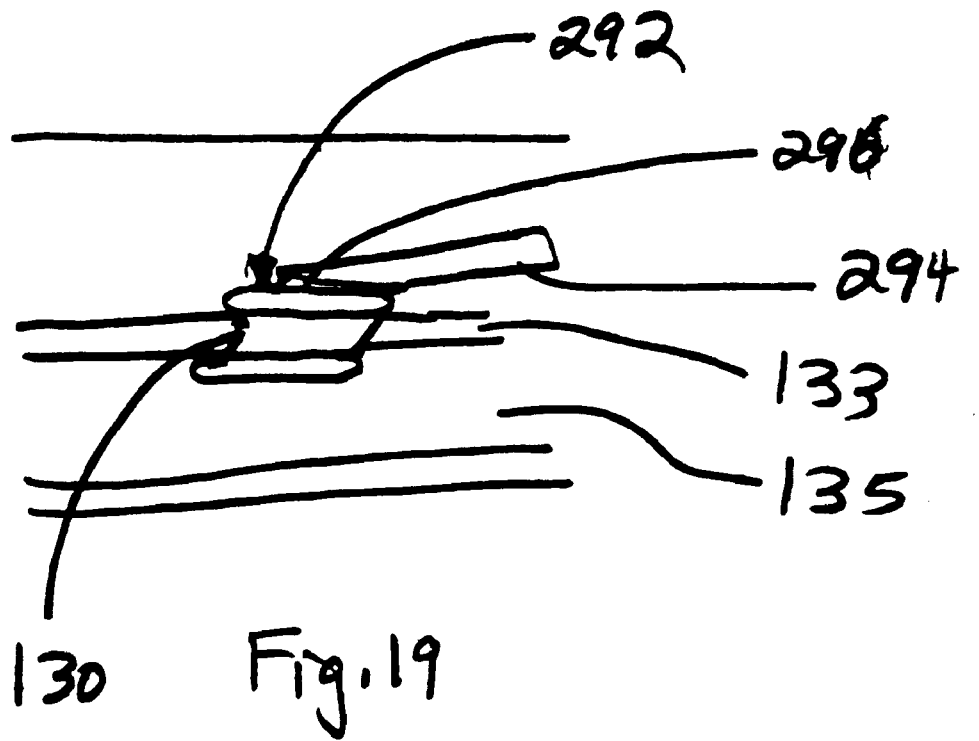
FIG. 19 is a side view of an angled arterial closure device having a foldable extending member.
Figure 42:
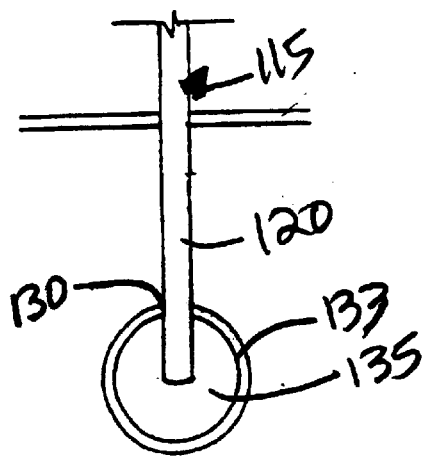
FIG. 42 is an end view showing the distal end of the introducer inside a vessel.
Figure 44:
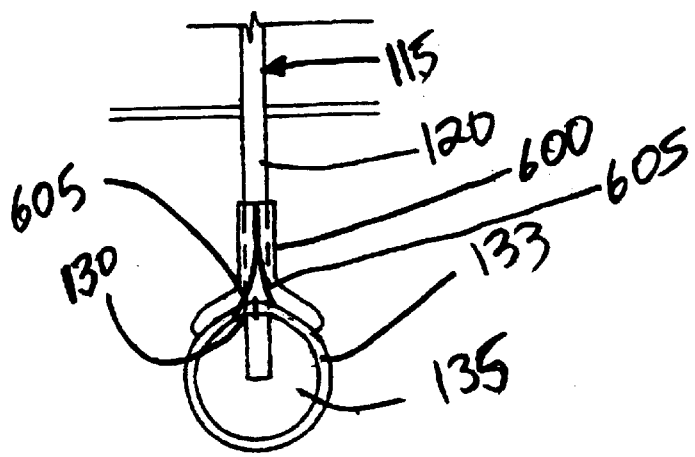
FIGS. 43 and 44 are end views showing a flared arterial closure device deployed along the introducer.
Figure 45:
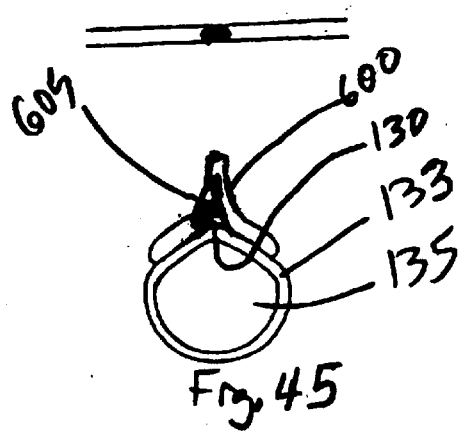
FIG. 45 is an end view showing the flared arterial closure device of FIG. 43 deployed against the vessel to close the arteriotomy.
Figure 43:
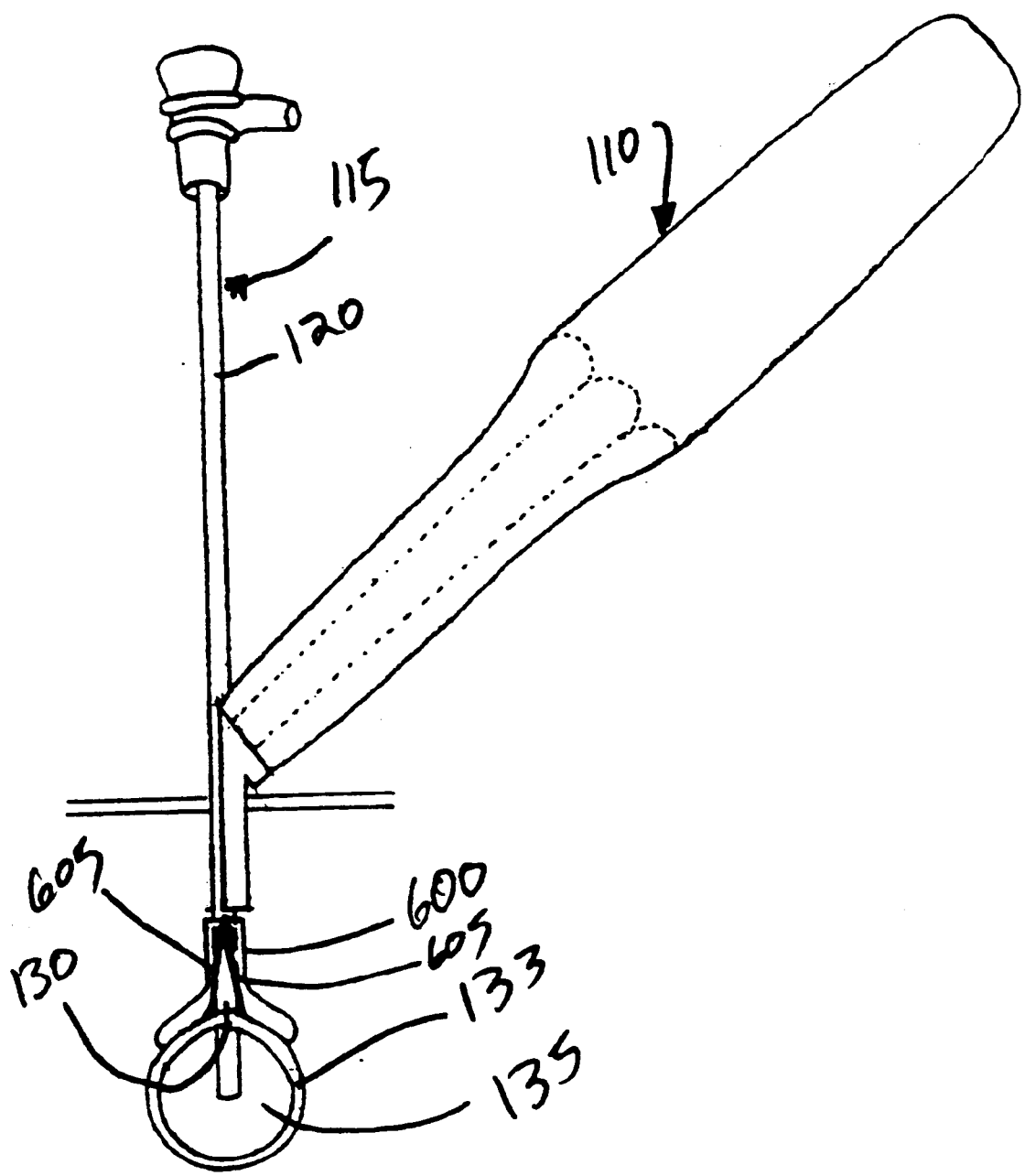

The geometry of the ACDs described herein is shown for illustration purposes as being generally round. However, they can be of any other geometry, such as oval, elliptical, rectangular, square, ridged, or a combination of shapes. The ACD has been illustrated as forming a generally perpendicular angle with the vessel wall once deployed. Nonetheless, the inventors intend the configuration to be at any suitable angle, such as between 30° and 60°, or, for example, 45° or as otherwise desired. A range of angles of the ACD can be available and the physician can choose the appropriate ACD based on the angle at which the introducer is introduced into the vessel. For example, referring to FIG. 18, a ACD 290 is formed to have the extending member 155 extending at an angle of approximately 45° from the second member 145. In addition, the first member 140 and the second member 145 are longitudinally offset. This configuration is designed to cause the extending member 155 to follow the path created by the introducer. Referring also to FIG. 19, the ACD has a second member 292, a foldable extending member 294, and a groove 296 positioned between the second member 292 and the folding extending member 294. In this manner, the extending member 294 can be folded or bent over to be less obtrusive and to close off the flow of blood through the ACD.

Referring to FIGS. 20–22, a deployment tool 300 is designed to engage or otherwise contact the proximal edge, or other edge, of the ACD. The tool 300 is generally handheld and includes a handle 305, an extension 310, and a contacting section 315 that clips onto, or otherwise contacts the outside of the introducer and mates with the ACD. The contacting section 315 has sufficient length to advance the ACD through the tissue to the desired position on the vessel. The handle 305 or grasping section can be, for example, round, rectangular, elliptical, or a combination of shapes or other shape that fit comfortably in the hand. The contacting section 315 can have a cross-sectional geometry of a partially open tube having more than 50% diameter coverage, so that it can clip onto, and slide over the outer diameter of the introducer.

Referring also to FIGS. 23–35, the deployment tool can include an additional extension 320 that is configured to fit around the extending member 155 and mate with the second member 145. The extension 320 can be attached to the introducer after the introducer is positioned within the artery.

The deployment tool 300 can be made partially or completely from several different polymer materials including polycarbonate, nylon, polyethylene, polytetrafluoroethylene (PTFE), fluoroethylene-propylene (FEP) or polyfluoroacrylate (PFA), polyester ether ketone (PEEK), polyamide, polyimide, polyethyleneteraphthalate (PET), combination or other material able to withstand sterilization processing. The tool can also be made partially or completely from several different types of metals including stainless steel; spring metal alloys such as elgiloy™, inconel™; superelastic/shape memory alloys such as Nitinol (NiTi) as well as composites and combinations thereof and combinations of other materials.

The deployment tool 300 can be made using several methods and processes including extrusion, molding (injection and other), casting, adhesive bonding, ultrasonic welding as well as combinations thereof and combinations of other methods and processes.

Modifications of the deployment tool 300 are possible. For example, the proximal edge of the ACD (i.e., of the extending member 155 or the second member 145) and the distal edge or other portion of the advancement tool 300 may have interlocking geometries to aid and/or control the position of the ACD during advancement along the introducer. The engagement/contact section 315, 320 of the tool 300 may have a cross-sectional geometry of a complete circle that is designed to split away from the introducer once the ACD has been advanced and deployed. Splitting can be accomplished by having weakened areas in the wall of the tubing, such as linear perforations, or linear scores. This version would require that the deployment tool be back loaded onto the introducer before the ACD is placed onto the introducer and prior to insertion into the vessel.

The inside, concave section of the contact section 315, 320 may be coated with a hydrophilic or other lubricious material to reduce the friction during advancement and deployment of the ACD. In addition to the deployment tool 300 contacting the proximal edge of the ACD, the contacting section 315, 320 of the tool can be lengthened and designed to further attach to and compress the distal edge of the ACD, thereby providing additional support during insertion and deployment into the vessel.

Referring to FIGS. 26–29, a ACD 350 includes a first angled closure edge 355, a second angled closure edge 360, an extending member 365, and a connection member 370 between the first and second angled closure members. The first angled closure edge 355 and the second angled closure edge are generally directed at each other such that they define a narrow opening 375 through which the vessel wall 133 is received. The ACD 350 is deployed over the introducer tube section 120 using, for example, the deployment tool 300. As illustrated in FIG. 28, the second angled closure edge 360 is deflected away from the first angled closure edge 355. The deflection can be caused, for example, by the contacting section 320 surrounding the second angled closure edge 360. In this manner, when the deployment tool 300 is removed, the second angled closure edge 360 deflects back to compress the vessel wall 133 between the angled closure edges 355, 360. The angled closure edges 355 and 360 are formed, for example, from a flexible member, such as a polymer, superelastic/shape memory material, or a combination of the two. For example, the superelastic/shape memory member can be coated with a polymer.

Referring to FIGS. 30 and 31, a ACD 400 includes a threaded section 405 and an extending section 410. The threaded section 405 includes threads 415 mounted on and between a first member 420 and a second member 425. The extending section 410 includes a longitudinal channel 430 that includes a distal shaped channel 435. A deployment tool having a mating shaped distal end is inserted into the longitudinal channel 430 such that it mates with the distal shaped channel 435. By rotating the deployment tool, the ACD can be threadably inserted into the arteriotomy.

In general, the distal edge of the ACD 400 is designed to engage the opening of the arteriotomy or puncture site and protrude to a specific depth based on how many times the ACD was advanced, twisted or turned. The ACD 400 may have a stop 437 to limit how far the device protrudes into the vessel. The same "screw" type distal edge could be used on a hemostatic plug, made from a solid piece of material, rather than a tube structure. A deployment tool would be needed that has, for example, a grasping distal end for insertion into the vessel.

The ACD 400 can be modified to include a longitudinal channel that pass through the entire length of the device and deployed over a introducer. In this case, the deployment tool and the proximal edge of the ACD would have a mating geometry such that the deployment tool is rotated to threadably insert the ACD through the arteriotomy.

Referring to FIGS. 32 and 33, a ACD 450 includes a tissue contacting member 455 and an extending member 460. A longitudinal channel 463 passes through the ACD. The extending member 460 includes a longitudinal slot 465 and a circumferential channel 470 in which a contracting member 475 is received. The contracting member 475 tends to close the longitudinal channel 463 unless kept open, for example, by an introducer 115 within the channel. In this manner, when the ACD 450 is deployed within the arteriotomy and the introducer is removed, the longitudinal channel is closed, which prevents or limits blood flow or seepage through the channel. The ACD can be formed from any of the materials described above. For example, the ACD can be formed from a polymer and the extending member can be formed from a flexible material such as a polyurethane/Dacron composite that easily collapses as a consequence of contraction property of the contracting member 475.

Referring to FIGS. 34 and 35, a ACD inner liner 480 is formed as a simple slotted tube 485 that includes a slot 490 along its length that functions a means for side access onto the introducer, after the introducer has been inserted into the vessel. The slot 490 can be formed as a longitudinal or radial slit, illustrated below. The ACD inner liner can be opened sufficiently to attach onto the introducer from the side. Any configuration of the ACDs described herein is built around the ACD liner 480 with a slot formed within the ACD. The tube 485 optionally can extend from the ACD and then be clamped at the proximal end once the ACD liner 480 and ACD are deployed.

Referring to FIGS. 36 and 37, a ACD liner 500 includes a tube 505 that includes a radial slot 510 along an extending member 515 through a first member 520 and a second member 525. The ACD inner liner 500 is sufficiently openable to be threaded onto the introducer from its side. Any configuration of the ACDs described herein can be built around the ACD liner 500 with a slot formed within the ACD. The tube 505 optionally can extend from the ACD and then be clamped at the proximal end once the ACD liner 500 and ACD are deployed.

Referring to FIGS. 38–41, a plug style ACD 550 that is similar to ACD 105 includes a channel 555 into which a deployment tool 552 is inserted to deploy the ACD through an arteriotomy to close the arteriotomy. The ACD includes an adhesive layer 560 for bonding to the tissue. The ACD 550 differs from the ACD 105 in that the channel 555 does not extend the entire length of the ACD. A ACD 570 (FIG. 39) is similar to the ACD 550 except that it has limited vessel protrusion, similar to the ACD 200 above. The ACD 550, 570 is placed into the arteriotomy and held briefly for an adhesive bond to form. The deployment device 552 then can be removed.

The distal end of the deployment tool 552 also can have a grasping feature to grasp the proximal end of the plug ACD during deployment and to release after the plug ACD has been seated in or is on the vessel, and able to release when the tool is being withdrawn.

Referring to FIGS. 42–45, a ACD can have a distal end geometry, which once positioned at the puncture site, is designed to compress the vessel wall for increased securement and sealing. For example, a ACD 600 may have a flare 605, or two or more longitudinal slits in the side of the tube, that are designed to open, or flare apart when advanced and in contact with the top of the vessel puncture site (i.e., arteriotomy). The ACD 600 can be made from a very elastic material and/or a superelastic/shape memory material such that when the introducer is removed, the flares or slits will pinch, or otherwise bring the edges of the punctured vessel together, effectively creating hemostasis. The inside of the flared section of the closure device could have biocompatible contact adhesive, other bonding material, and/or small barbs or protrusions that may assist in securing the device to the top of the vessel wall.

Figure 46:
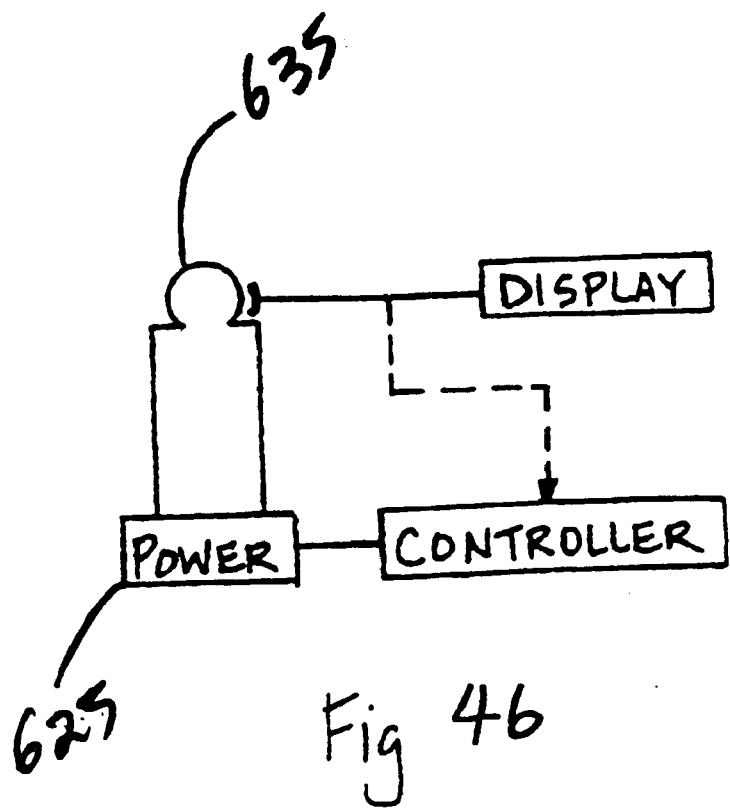
FIGS. 46 and 47 are electrical schematics for a direct resistive element heating circuit and an ohmic tissue heating circuit.
Figure 47:
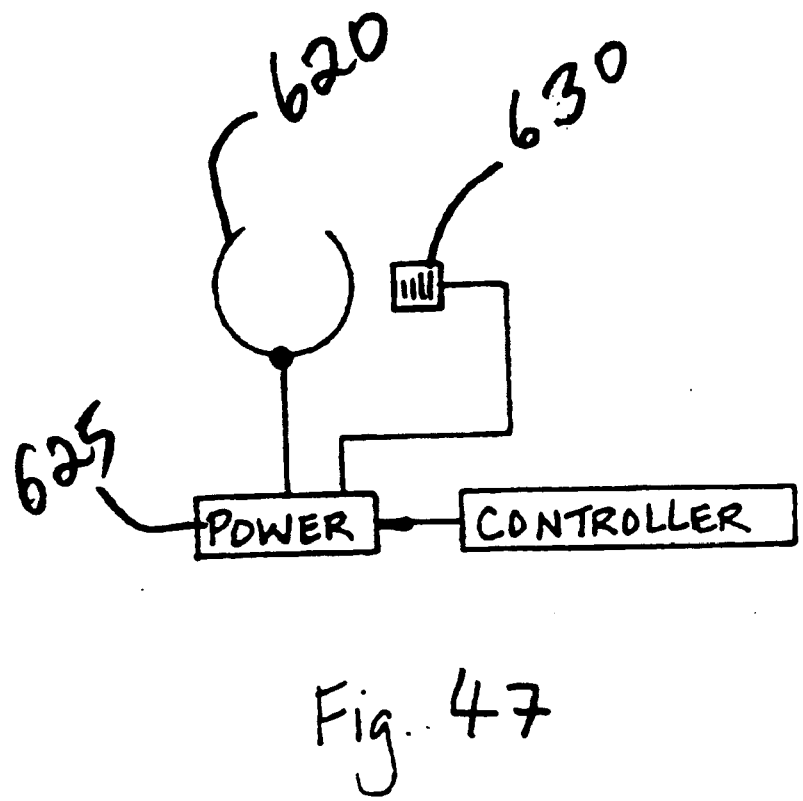
Figure 48:
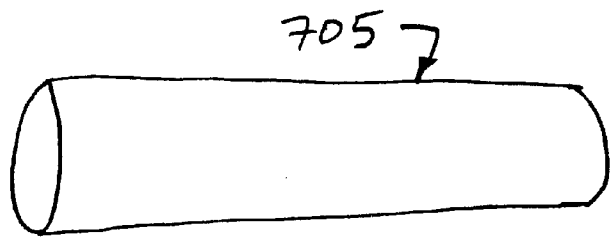
FIG. 48 is a perspective view of a tube used to fabricate a arterial closure device.
Figure 49:
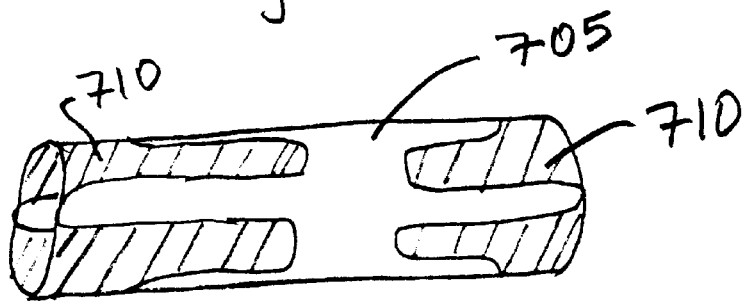
FIG. 49 is a perspective view of the tube of FIG. 48 showing material being removed.

Referring to FIGS. 46 and 47, heat can be used to assist with, or as an adjunct to, the process by recovering the ACD, activating (e.g., causing to flow, etc.) a hemostatic material to the puncture site that assists in sealing (e.g., through vessel contraction including the denaturing and reformation of collagen at the site) or accelerate healing, or a combination of these or other beneficial effects. Direct resistive element heating (FIG. 46) or ohmic tissue heating (FIG. 47) can be utilized. Biocompatible electrode materials (e.g., gold, platinum, and other suitable materials) can be mixed with the base material of the ACD as a powder during manufacturing, or as a wire, strip, or other geometry, added onto any surface of the device, and connected to a suitable (i.e., electrical and biocompatible) conductor. For ohmic tissue heating, one end of the first conductor 620 is connected to an RF power source with the other end connected to an electrode, as illustrated in FIG. 47. Another conductor is connected to a ground pad 630 placed on the patient's body, and also connected to the power source. For direct resistive element heating, both conductors from the power source 625 are connected to an electrode 635. Once the sealing of the puncture site has occurred, a twisting, cutting, or other manipulative action removes the conductor previously attached to the closure device. Alternatively, a special tip is placed over a standard electro surgical tool (e.g., Bovie) to insert through the skin and make contact with the closure device, tissue or both.

Alternative versions of the closure device may utilize an electrode that is formed by ion deposition, sputter coating, spraying, dip coating, adhesive, combination or other method or design.

Figure 50:
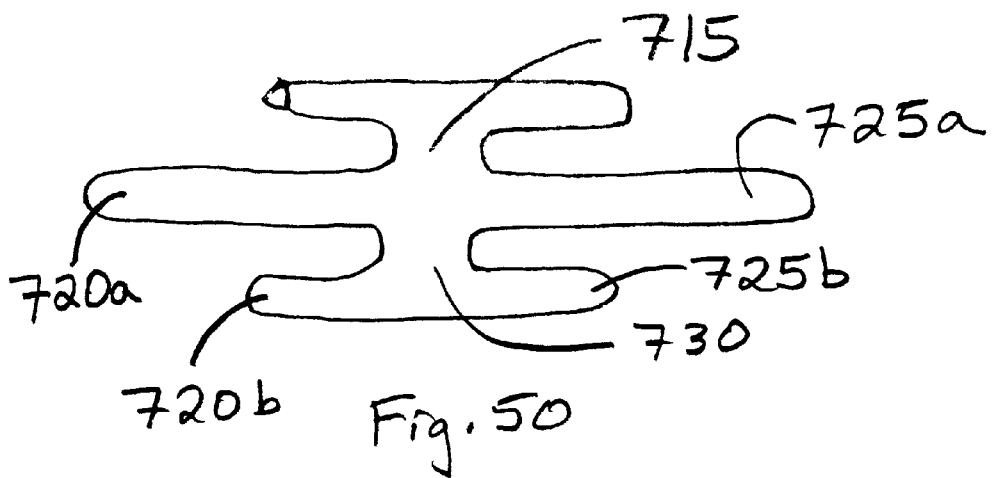
FIG. 50 is a side view of the tube of FIG. 48 with the material removed.
Figure 51:
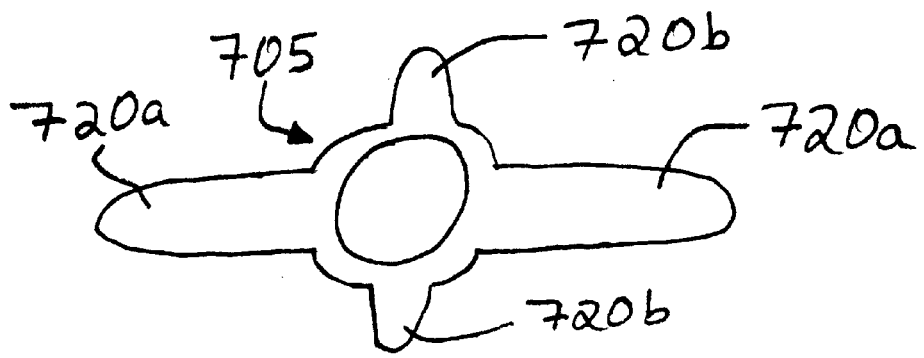
FIG. 51 is a top view of the curved configuration.
Figure 52:
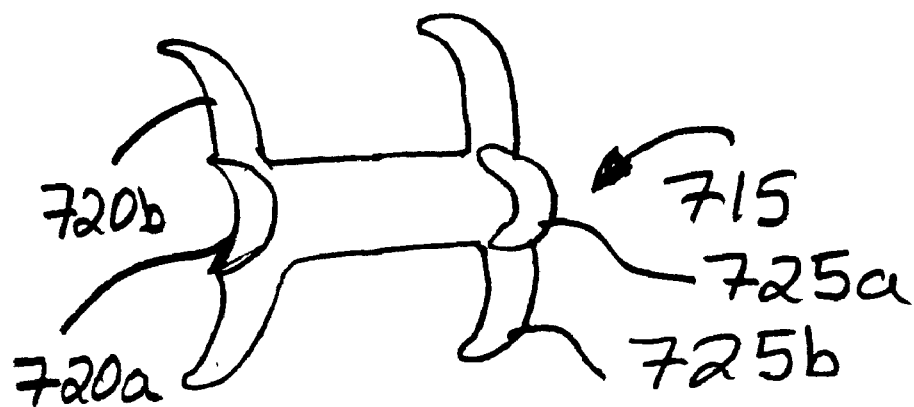
FIG. 52 is a side view of the configuration of FIG. 51.
Figure 53:
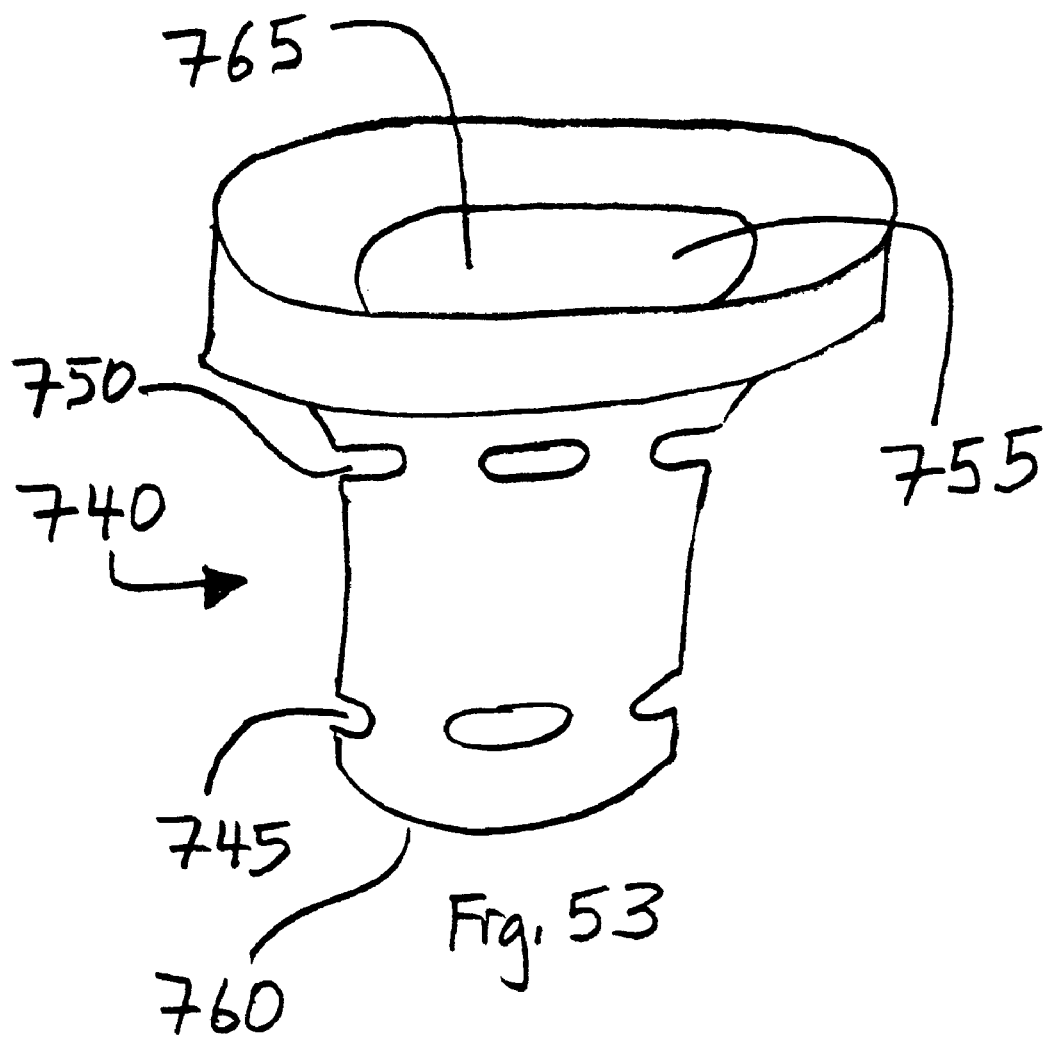
FIG. 53 is a perspective view of a fabric covering.

Referring to FIGS. 48–58, a superelastic/shape memory ACD 700 is made from a superelastic/shape memory sheet or tube 705. The sheet or tube 705 is etched, cut, or otherwise machined to remove material 710 (FIG. 49) to leave a starting configuration 715 (FIG. 50). The method of removing the material may be, for example, photo-etching and/or laser or chemical cutting. The starting configuration includes first extending members 720, second extending members 725, and a connecting member 730 between the first and second extending members. The first and second extending members 720 and 725 then are bent and curved (FIGS. 51 and 52). The first and second extending members are curved to mate with the inner and outer surface, respectively, of a vessel. For example, longer first and second extending members 720a and 725a are bent to be generally perpendicular to the connecting member 730 and have a curvature that is similar to that of the length dimension of a vessel wall. The shorter first and second extending members 720b and 725b are bent to have a radius of curvature that is similar to that of the radius of curvature of the circumference of a vessel wall. The shapes of the first and second extending members 720, 725 are set using known techniques of imparting shapes in superelastic/shape memory materials, as described in further detail below.

Figure 54:
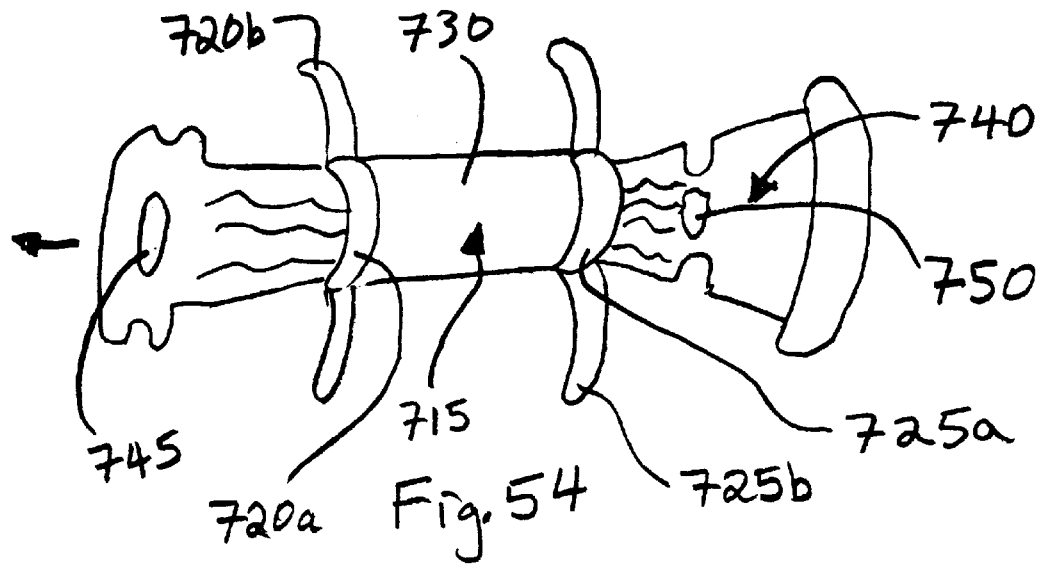
FIGS. 54–58 are side views showing the fabric covering of FIG. 53 being mounted within the curved configuration of FIG. 51 to form a arterial closure device.
Figure 55:
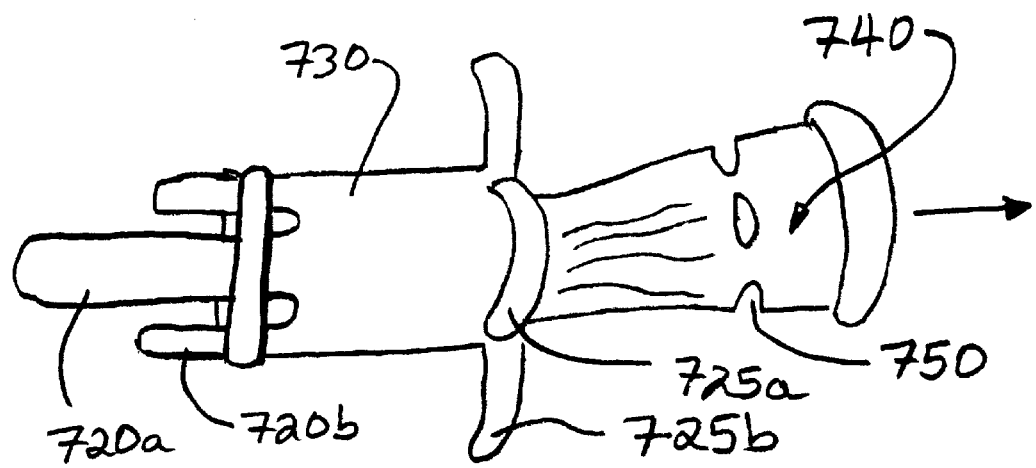
Figure 56:
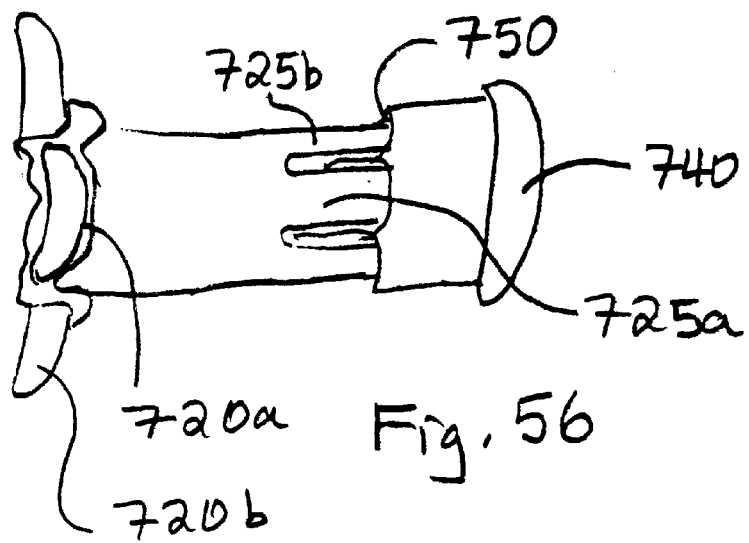
Figure 57:
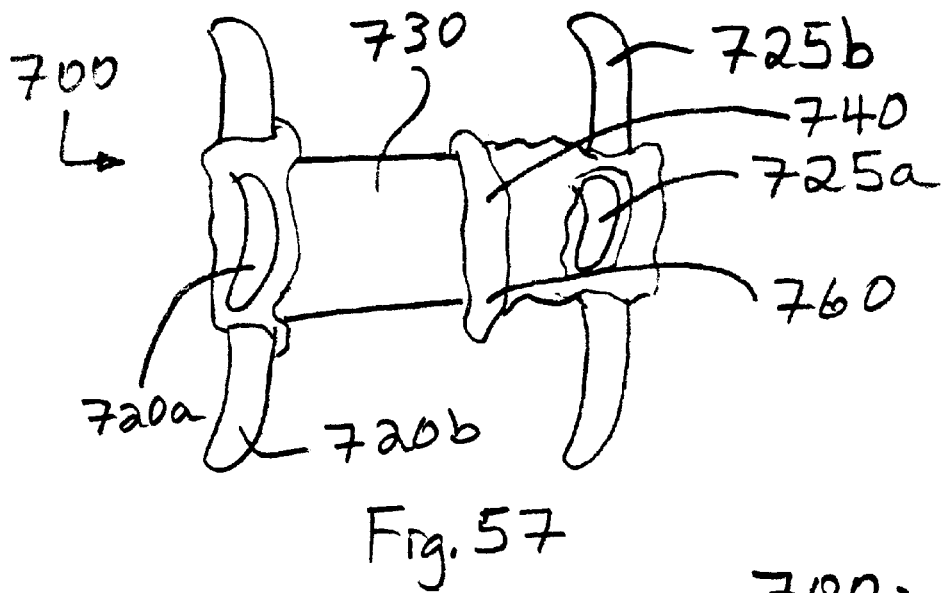
Figure 58:
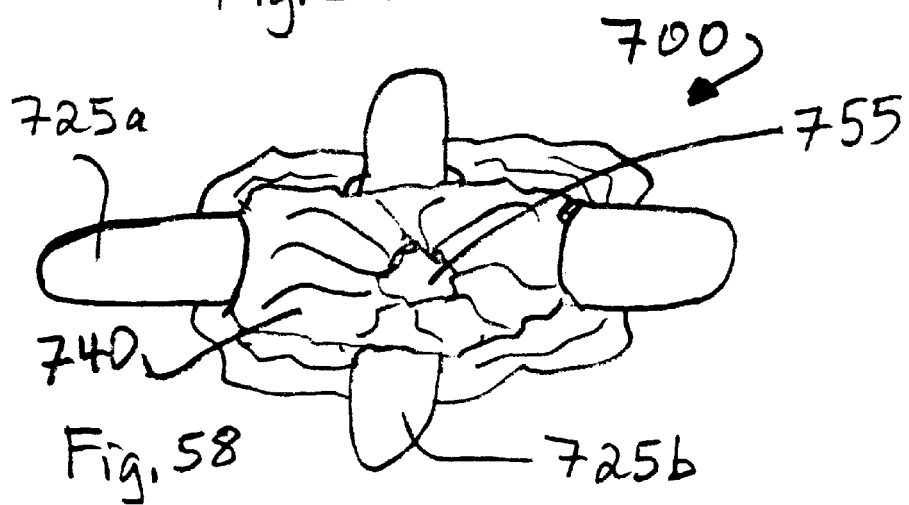

A fabric covering 740 (FIG. 53), such as Dacron, then is mounted to the curved configuration 715. The covering 740 includes distal side openings 745 and proximal side openings 750. A longitudinal channel 755 passes between a distal opening 760 and a proximal opening 765. The covering 740 is pulled distal end through the curved configuration 715 and the extending members 720 are straightened from their retracted state and passed through the distal side openings 745 (FIG. 54). The covering 740 then is pulled back such that the distal side openings 745 are tight against the first extending members 720 (FIG. 55). The first extending members 720 then are allowed to expand back to their retracted state. The second extending members 725 then are straightened from their retracted state and passed through the proximal side openings 750 (FIG. 56). The second extending members 725 then are allowed to expand back to their retracted state, thereby trapping a proximal end 760 of the covering against the connecting member 730 between the first and second extending members 720, 725 (FIGS. 57 and 58). The longitudinal channel 755 passes through the covering 740 and the shaped configuration 715.

Referring to FIG. 59, the second extending members 725b can be configured to curve back over and under the opposite second extending member 725b. Thus, instead of curving against the outer circumference of the vessel in which the device is implanted, the second extending members 725b function to close the longitudinal channel 755 when they are in their retracted position. The covering 740 is mounted to the curved configuration 715 as described above. The second extending members 725*b* are kept in a straightened position because of the introducer or catheter that passes through the longitudinal channel 755. When the introducer or catheter is removed, the second extending members 725*b* return to their retracted position, thereby closing or partially closing the longitudinal channel 755. The covering 740 also contributes to the closure of the longitudinal channel 755 and reduction or elimination of blood leakage or seepage through the longitudinal channel.

Figure 62:
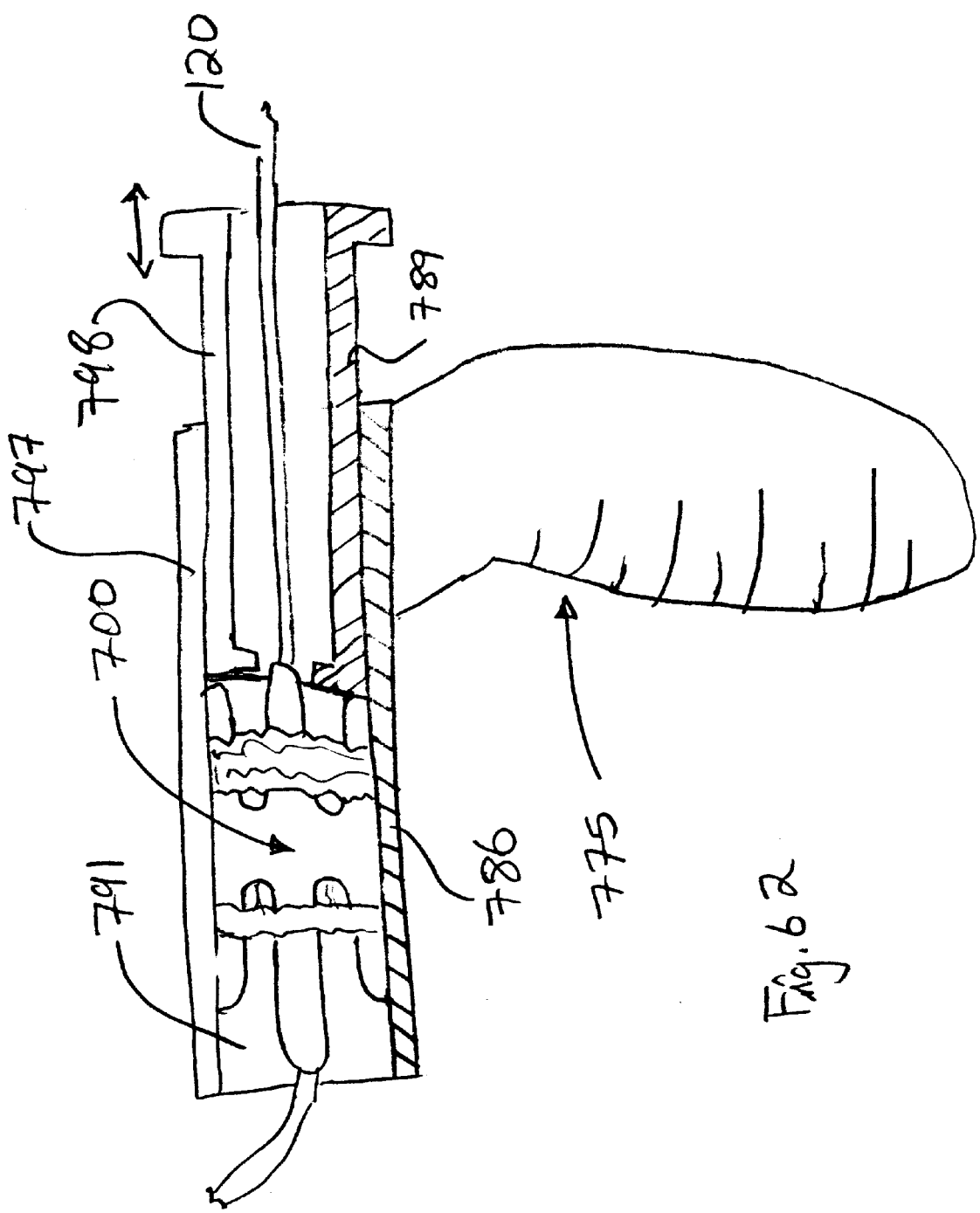
FIG. 62 is a cross-sectional side view of the deployment tool of FIG. 60 having the arterial closure device within.

Referring also to FIGS. 60–62, the ACD 700 is deployed using a deployment tool 775. The deployment tube includes a handle 780, an extension 783, a guide 786, and a pusher tuber 789. The guide 786 extends from the extension 783 and includes a first longitudinal channel 791 and a longitudinal ridge 792 that passes along the inner surface of the first longitudinal channel 791. The pusher tube 789 is slidably mounted within the first longitudinal channel 791 and includes a second longitudinal channel 793, a pusher surface 794, and a groove 796 that is configured to slide over the longitudinal ridge 792. The guide 786 and the pusher tube 789 include longitudinal slots 797, 798 so that the deployment tool 775 can be placed around the catheter or introducer. With the ACD 700 positioned over a catheter or introducer 120, and positioned within the longitudinal channel 791 in the guide 786, the physician pushes the ACD 700 along the introducer 120 into the vessel using the pusher tube 789. Of course, the ACD can be placed within an arteriotomy using other deployment tools or even by hand.

Referring to FIGS. 63*a*–63*j*, the ACD can be configured as a hemostatic patch or collar that surrounds an opening in a tubular vessel, such as an arteriotomy. As described in more detail below, the patches include means to attach to or conform to a tissue surface or tubular organ to seal, close, or reinforce an opening. The patch is generally simple to use, inexpensive, and effective at providing hemostatic sealing. The patch can be used for several different applications in the body, including, but not limited to, percutaneous vessel access closure as an arteriotomy closure device ("ACD"). The patch is part of a system that includes two main components, a compliant, atraumatic biocompatible patch or collar and a deployment device. The hemostatic patch/collar is attached or loaded onto the distal end of the deployment device. Once the vascular introducer, catheter, or other device has been removed from the vessel, the hemostatic patch/collar can be advanced through the skin to the puncture site on the vessel and secured into place using the deployment device. The patch/collar can be secured to the vessel with adhesives, a compressive force, as described below, a combination of these or other suitable attachment means.

Figure 63A:
FIGS. 63a–j are top views of patches/collars.

Specifically, FIG. 63*a* illustrates a patch 800 that includes an opening 805 and a slit 810. The patch 800 can be passed over a device that is inserted into a tubular body opening to provide a temporary or permanent seal between the tubular body and the device within the tubular body. Similarly, the patch can have a longitudinal tubular geometry and/or have an opening of sufficient size through the thickness of the patch to be used as a conduit or conduit reinforcement device. The cross section can be consistent or tapered. A deployment device with a grasping and releasing distal end, described below, may be used to position and deploy this version of the patch.

Figure 63B:
Figure 63C:
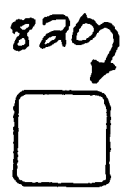
Figure 63D:
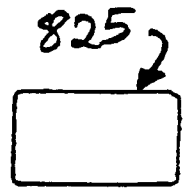
Figure 63E:
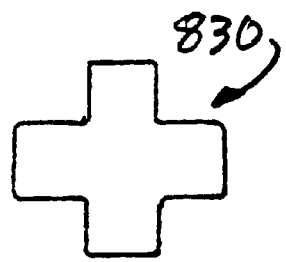
Figure 63F:
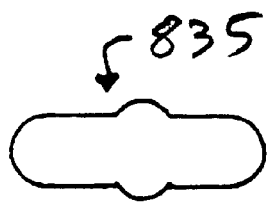
Figure 63G:
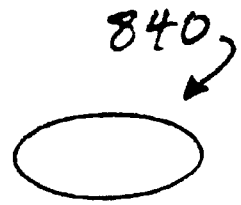
Figure 63H:
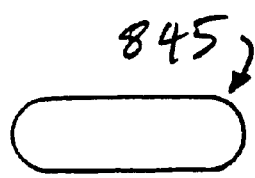
Figure 63I:
Figure 63J:

FIG. 63*b* illustrates a small, oval shaped patch 815 that can be placed over an opening in a tubular vessel. The patch 815 can be oriented lengthwise or widthwise to the tubular vessel. FIG. 63*c* illustrates a square shaped patch 820 that can be placed over an opening in a tubular vessel. FIG. 63*d* illustrates a rectangular patch 825 that can be placed over an opening in a tubular vessel. The patch 825 can be oriented lengthwise or widthwise to the tubular vessel. FIG. 63*e* illustrates a cross-shaped patch 830 that can be placed over an opening in a tubular vessel. The patch 830 includes legs that encircle the vessel and legs that run the length of the vessel. FIG. 63*f* illustrates a patch 835 that can be placed around the tubular vessel in two orientations depending upon the opening in the vessel. FIGS. 63*g* and 63*h* illustrate large, oval patches 840, 845 that can be placed around the tubular vessel in two orientations—a lengthwise orientation and a widthwise orientation. FIGS. 63*i* and 63*j* illustrate round patches 850, 855 having legs that extend from a generally round center. The patch 850 has four legs that can wrap around the vessel and the patch 855 has six to eight legs that can wrap around the vessel.

Referring to FIGS. 64*a*–64*c*, the patches above, e.g., the patch 815, can have a single layer 856 (FIG. 64*a*), dual layer 856, 857 (FIG. 64*b*), or multi-layered, for example, having three layers 856, 857, 858 (FIG. 64*c*). Although the patch 815 is used primarily in the description below, this use is purely for explanatory purposes and is applicable to the other patches/collars described herein.

As illustrated in FIGS. 65*a*–65*d*, the patches above, e.g., the patch 815, can be of different sizes for providing various closure of the vessel opening. For example, FIG. 65*a* illustrates the patch 815 having a single layer 856 and a small size such that it covers only a small portion of the circumference of a vessel 860. FIG. 65*b* illustrates the patch 815 having two layers 856, 857 and a medium size such that it covers a larger portion of the circumference of the vessel 860 than does the patch of FIG. 65*a*. FIG. 65*c* illustrates the patch 815 having two layer 856, 857 and a larger size such that it covers almost the entire circumference of the tubular vessel 860. Finally, FIG. 65*d* illustrates the patch 815 being of a sufficient size and having two layers such that it encircles the entire circumference of the tubular vessel 860.

In use, the hemostatic patch/collar is designed to be of a sufficient size, shape, strength flexibility, and thickness for the purpose of closing an vessel or opening to, for example, provide hemostasis, particularly at a percutaneous vessel access puncture site. The properties of the patch, e.g., rigidity, flexibility, tissue closure compressive force, may be modified by varying one or more of the geometry, material, components, processing, or other characteristic of the patch.

As described above, the hemostatic patch/collar can be single or multiple layered. As described in more detail below, it also can be fabricated with or without a superelastic/shape memory component or other reinforcement that is capable of compression. These components or reinforcements can be one of the layers illustrated above. As also illustrated above, several different geometries can be used, including, but not limited to round, rectangular, triangle, "X", cross, combination or other geometry. The thickness of the patch/collar may be the same throughout or vary as desired by the physician. The tissue contacting surface may be flat, smooth, irregular, woven, or include dimples or protrusions. These surface configuration can be selected for several purposes including bonding, securing, tissue growth, etc. The patch or collar may also have one or more hole, pores, grooves, slots, or opening that pass partially or completely through the patch or collar. The opening are provided for several reasons, including to reinforce the device or to act as a strain relief for a conduit, and to allow nutrients to reach the vessel (or tissue) surface. For nutrient access, one, but not the only, range of hole size is between 30 and 250 microns in diameter.

The tissue contacting surface of the hemostatic patch/collar can have a coating or layer of a biocompatible contact adhesive, or other material to bond or secure the patch/collar to the vessel to better seal the puncture site or opening. For example, the adhesive layer can be layer 856 of FIGS. 64b and 64c. The bonding materials can be added during the manufacturing process or just prior to use. The bonding materials could be in the form of a liquid, semi solid, or solid. Suitable bonding materials include gels, foams and micro-porous meshes. Suitable adhesives include acrylates, epoxies, fibrin-based adhesives, UV light activated adhesives and/or heat activated adhesives and other specialized adhesives. The adhesive can be selected to bond on initial contact, or after a longer period to allow repositioning if desired. One effective adhesive is a crystalline polymer that changes from a non-tacky crystalline state to an adhesive gel state when the temperature is raised from room temperature to body temperature. Such material is available under the trade name Intillemer™ adhesive, available from Landec Corp. Composites and combinations of these materials also can be used.

The hemostatic patch/collar can be partially or completely fabricated from many different types of biocompatible materials, including expanded polytetrafluoroethylene ("ePTFE"), polyester, woven Dacron, polyurethane, silicone, a composite material, or a combination of these or other suitable materials. Some polymer materials could be irradiated in a desired geometry, for the shape to be "set" into that position. This setting is advantages if it is helpful to provide a particular profile to vessel. For example it may be helpful to provide a compressive force to the vessel once the patch/collar is deployed around the vessel. A similar process using heat instead of radiation can be used to anneal the polymer and then cool the polymer into a particular shape.

The patch/collar also can be partially or completely made from many different types of biodegradable/bioabsorbable materials, including modified starches, gelatins, cellulose, collagen, fibrin, fibrinogen, elastin or other connective proteins or natural materials, polymers or copolymers such as polylactide [poly-L-lactide (PLLA), poly-D-lactide (PDLA)], polyglycolide, polydioxanone, polycaprolactone, polygluconate, polylactic acid (PLA), polylactic acid-polyethylene oxide copolymers, poly(hydroxybutyrate), polyanhydride, polyphosphoester, poly(amino acids), poly(alpha-hydroxy acid) or related copolymers of these materials as well as composites and combinations thereof and combinations of other biodegradable/bioabsorbable materials.

Additionally, the patch/collar can be partially or completely fabricated from materials that swell, or expand when they are exposed to a fluid, such as blood, other body fluid, or other fluid that can be applied in use. These materials include hydrophilic gels (hydrogels), foams, gelatins, regenerated cellulose, polyethylene vinyl acetate (PEVA), as well as composites and combinations thereof and combinations of other biocompatible swellable or expandable materials.

The hemostatic patch/collar can be fabricated using several methods and processes including extrusion, molding (e.g., injection molding or other known molding techniques), casting, laminating, dip coating, spraying, as well as combinations of these and other methods and processes. The patch/collar material can be formed into various geometries by die cutting or other similar methods.

Figure 66:
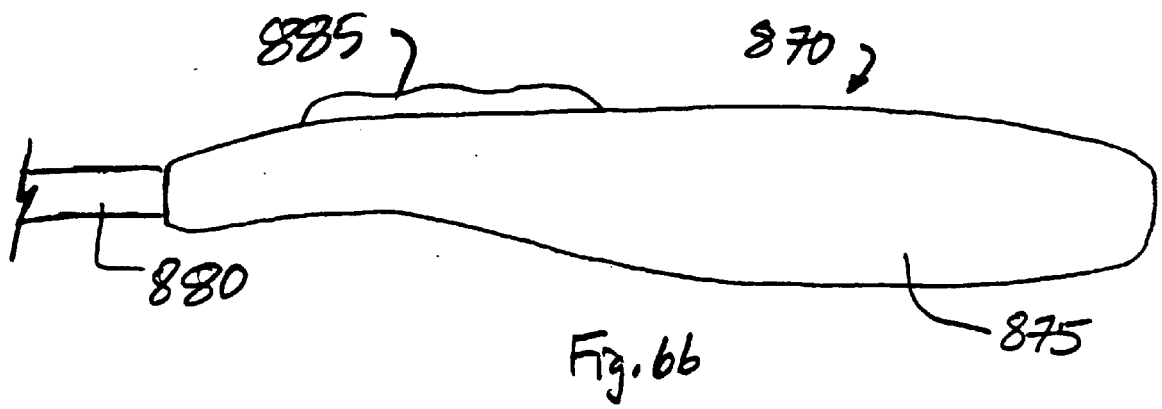
FIG. 66 is a side view of the handle of a deployment device.
Figures 67A, 67B, 67C:
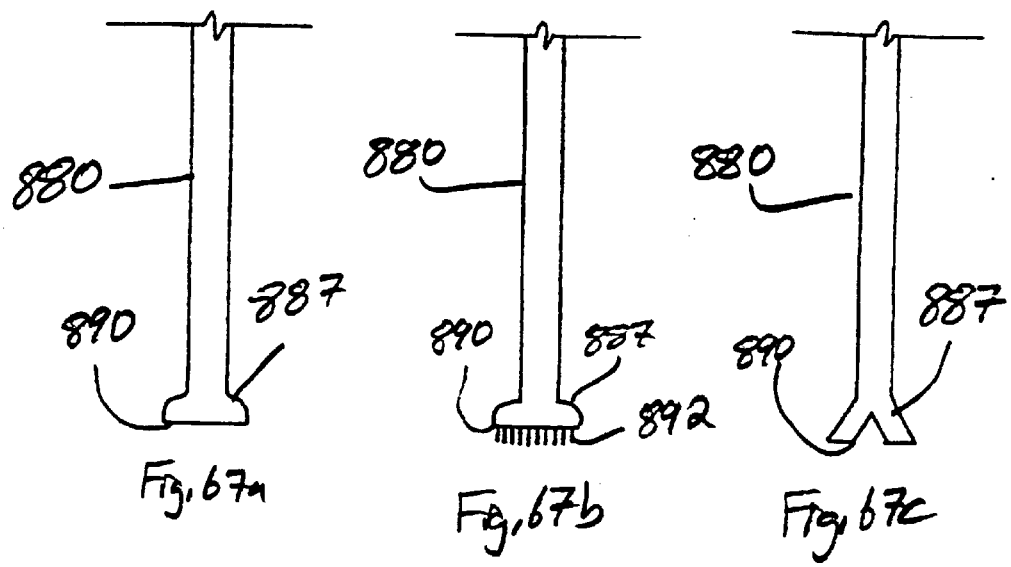
FIGS. 67a–c is a side view of the distal end of the deployment device of FIG. 66.

The patches/collars described above can be placed on a vessel by hand or by using a deployment device. Referring to FIG. 66, a deployment device 870 includes a handle 875 and a deployment section 880. The handle 875 includes a finger activated switch 885 that is used in deploying the patch/collar from the deployment section 880. The handle 875 can be round, rectangular, elliptical, combination or other ergonomic shape to fit comfortably in the hand of the physician. Referring also to FIGS. 67a–67c, the deployment section 880 includes a distal end 887 that includes a distal surface 890. The patch/collar is mounted to the distal surface 890 during deployment of the patch/collar. The distal surface 890 can be of any shape and may or may not be configured to match the geometry of the patch/collar that is to be deployed using the device 870. Either section of the deployment device may be straight or curved, rigid or flexible, or a combination of these shapes.

In particular, FIG. 67a illustrates a flat, distal surface 890 to which the patch/collar may be applied through a weak adhesive. For example, a weak adhesive can be applied to the distal surface 890 and the patch/collar is then pressed against the surface 890. To deploy the patch/collar, the physician uses the deployment device to press the patch/collar against the vessel wall. Because the patch/collar has an adhesive surface that is presses against the vessel wall, the patch/collar will have a tendency to remain attached to the vessel wall. By then sliding the deployment device laterally relative to the vessel, or rotating the device, the weak adhesive between the deployment device and the patch/collar will release and the patch/collar will remain attached to the vessel wall.

FIG. 67b illustrates the distal surface 890 as having a series of protrusions or barbs 892 against which the patch/collar is pressed to provide a weak attachment. Again, using the deployment device 870 to press the patch/collar against the vessel wall such that the adhesive on the patch/collar will adhere to the vessel wall. By then moving the device 870 laterally or rotating the device, the attachment of the patch/collar to the barbs 892 is released, and the patch/collar remains attached to the vessel wall.

FIG. 67c illustrates the distal surface 890 as having a concave pronged or forked configuration to which the patch/collar is attached. For example, the patch can have a strong adhesive on its tissue contacting surface and the distal surface 890 can have a weak adhesive applied. In this manner, when the deployment device is pressed against the vessel wall the patch will remain adhered to the vessel.

Figures 68A, 68B:
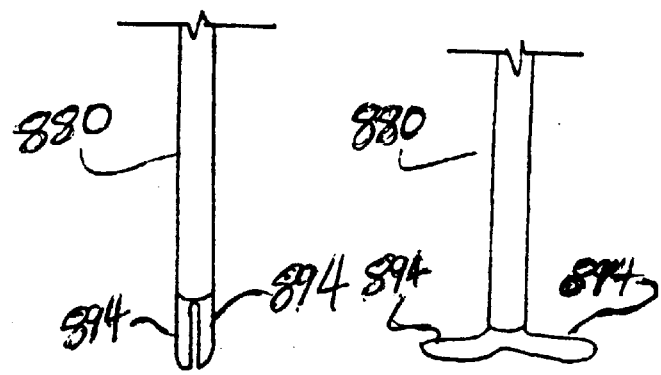
FIGS. 68a and b are side views of the distal end of the deployment device having openable jaws.

Referring to FIGS. 68a and 68b, the deployment device 870 can be designed to have a reduced profile during insertion and be expanded above the vessel prior to placing the patch/collar into contact with the vessel. For example, the deployment section 880 includes a pair of distal jaws 894 that are openable and closable. The jaws may be opened and/or closed by a pull wire, screw, stylet, or other means controllable from the proximal end or side of the deployment device. For example, the jaws 894 may be biased in a closed position (FIG. 68a) and the thumb switch 885 may be connected with a wire to the jaws such that retracting the thumb switch opens the jaws (FIG. 68b). The deployment device 870 may incorporate small barbs, a weak adhesive, local vacuum (e.g., with a bulb and valve in the manner used on a blood pressure cuff), or a vacuum line or tube connected to a remote vacuum source, a combination of these methods or other suitable methods for hold or retaining the patch/collar onto the bottom of the deployment tool during insertion to a securement site.

Referring also to FIGS. 69a and 69b, to use the jaws 894 with the deployment device, the hemostatic patch/collar 815 is folded onto itself during insertion, and opened, or spread by the opening of the jaws 894 prior to placement on the vessel. Of course, the collar/patch also can be placed on one jaw only and not be folded onto itself. In this configuration, opening the jaws, exposes the patch/collar on only one jaw such that only that jaw need be pressed against the site to which the patch/collar is to be positioned.

Referring to FIG. 70, the deployment device 870 may have the deployment section 880 configured to have a semi-circular distal surface 900 into which the patch/collar 815 is inserted. The patch 815 is retained in the distal surface 900 by any of the methods described above, including barbs, a weak adhesive, or vacuum. If an adhesive is used, pressing the patch against the vessel and then sliding the deployment device relative to the patch will break the adhesive bond between the patch and the distal surface 900. As illustrated in FIGS. 71*a* and 71*b*, a vacuum 903 also can be applied to a flat distal surface 905 and the patch/collar 815 retained to the deployment device in that manner. When deploying the patch, the physician presses the patch against the vessel and then removes the vacuum, thereby releasing the patch.

Referring to FIG. 72, a semi-circular configuration 910 that is similar to the semicircular distal surface 900 further includes a pair of prongs 915 to retain the patch. For example, if the patch has a tendency to expand outwardly, the prongs 915 will function even more advantageously to retain the positioning of the patch. To deploy the patch, the physician guides the deployment device 870 to the vessel and presses the patch against the vessel. Because the patch has an adhesive material or other type of material to adhere the patch to the vessel, the patch has a tendency to adhere to the vessel. Thus, to remove the deployment device from the deployed patch, the physician merely slides the deployment device lengthwise along the patch. Referring to FIG. 73, the deployment device 870 may also have an extendable plunger 920 or other type feature operable from the thumb switch 885 to separate, advance or deploy the patch/collar from the distal end 910 of the deployment device to the desired location on the vessel. For example, referring to FIG. 74, the distal end of the plunger 920 can include an extended semicircular surface 925 that advances the patch/collar out of the deployment device 870.

Figures 75A, 75B:
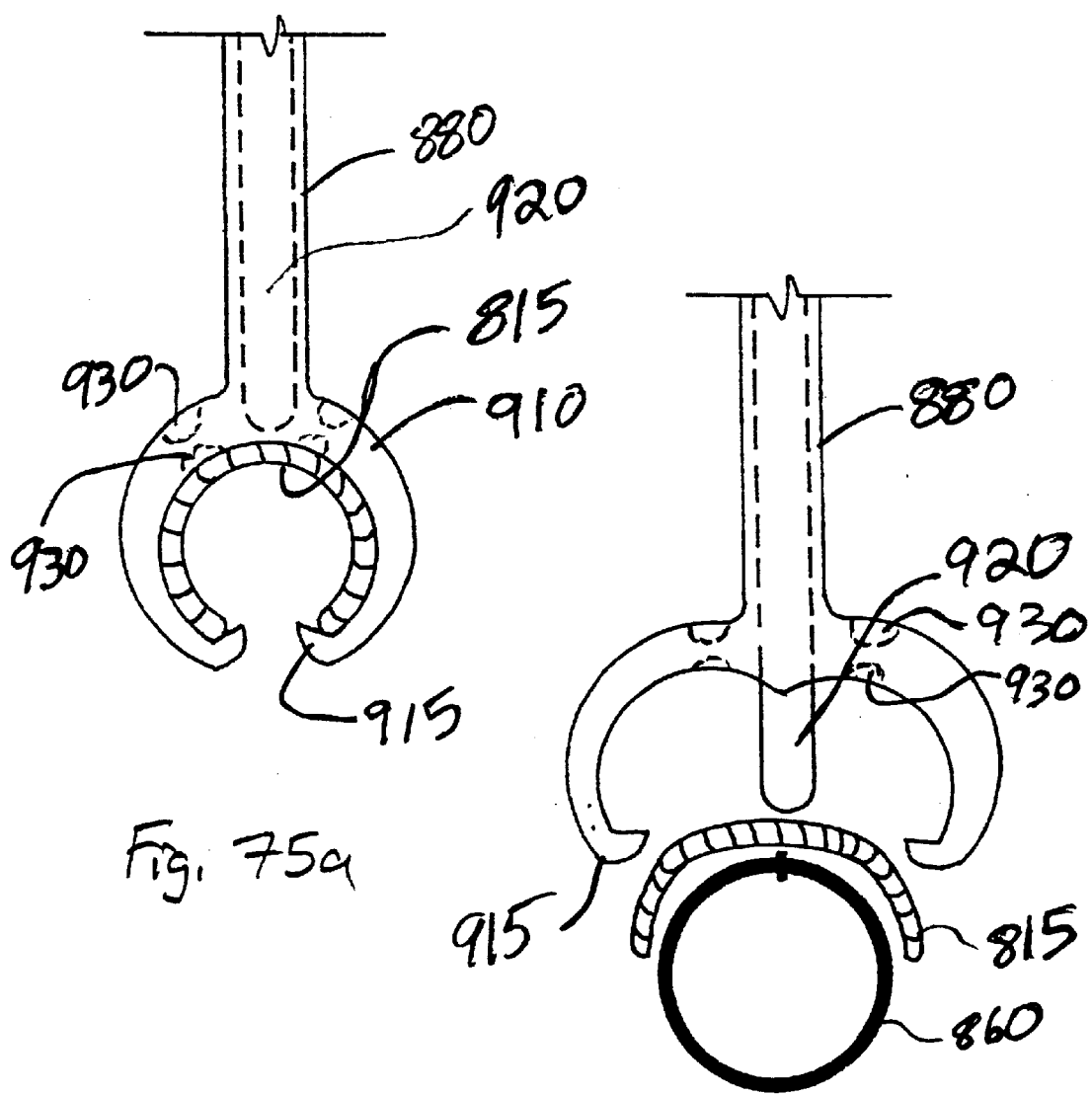
FIGS. 75a and 75b are side views of a combination deployment device with multiple features.

Referring to FIGS. 75*a* and 75*b*, the deployment device 870 can include one or more of the components described above. For example, the semi-circular configuration 910 can be hinged or flexible such that it opens outwardly. The plunger 920 can be operable with the configuration 910 such that operating the thumb switch 885 advances the plunger and opens the configuration 910. The prongs 915 help retain the patch/collar 815 within the configuration 910. The hinging of the configuration 910 may be implemented by using a weakened or narrowed section 930.

Additionally, the deployment device 870 may have a geometric shape designed to temporarily hold, compress or secure the patch or collar to the distal end of the deployment device prior to deployment. For example, the prongs 915 are one example of the implementation of the geometric shape.

The deployment device can be fabricated partially or completely from several different polymer materials including polycarbonate, nylon, polyethylene, polytetrafluoroethylene (PTFE), fluoroethylene-propylene (FEP) or polyfluoroacrylate (PFA), polyester ether ketone (PEEK), polyamide, polyimide, polyethyleneteraphthalate (PET), a combination of these materials or other suitable material that are capable of withstanding sterilization processing. The deployment device also can be made partially or completely from several different types of metals including stainless steel; spring metal alloys such as elgiloy™, inconel™; superelastic/shape memory alloys such as Nitinol (NiTi), as well as composites and combinations of these and other suitable materials. The deployment device can be made using several methods and processes including extrusion, molding (e.g., injection and compression), casting, adhesive bonding, and ultrasonic welding, as well as combinations of these and other suitable methods and processes.

The patch and the deployment device can be implemented in different configurations and with additional features. For example, the patch can be fabricated to include a radiopaque material, such as barium sulfate, bismuth trioxide, tantalum or other radiopaque. The radiopaque material can be added to the device itself, the reinforcement structure, or the bonding material.

The hemostatic patch/collar also may have the ability, once positioned at the puncture site, to compress the vessel wall for increased securement and sealing. This can be accomplished by making the patch/collar completely or partially from a very elastic material that is stretched while being secured to the vessel wall and allowed to recover after being secured to the vessel wall (i.e., when the deployment device is separated from the patch/collar). The elastic material may include or be a layer of a superelastic/shape memory material to assist with the closure or reinforcement. The recovery of the elastic material may be configured to cause the ends of the puncture site to plicate, or be brought together. Moreover, a biocompatible contact adhesive or other suitable bonding material and/or small barbs or protrusions can be used to assist bonding or securing the patch/collar to the top of the vessel.

Referring to FIGS. 76*a* and 76*b*, the hemostatic patch/collar 815, as well as the other patches described herein, may be configured to include a metallic component, such as a wire, rod, tube, coil, sheet, strip, band, in the middle, outer region, in between, side, of the patch/collar. The metallic material may be a superelastic/shape memory alloy such as Nitinol. The superelastic/shape memory alloy material may be annealed in one configuration during manufacture and processed and packaged in another configuration. As illustrated in FIGS. 76*a* and 76*b*, a shape memory alloy 935 is positioned within an inner layer 857 and surround by an upper layer 858 of a biocompatible polymer and a lower layer 856 of a biocompatible polymer. The polymer may be any of the polymers described herein, such as Dacron or PTFE. When a shape memory material is exposed to normal body temperature (37° C.), it will match the geometry and contract against the vessel, recovering to the optimum size and diameter. Alternatively, a superelastic material can be used in this same configuration. The superelastic material is initially deformed or deflected during deployment and then recovers its shape to match the geometry of the vessel. Superelastic component layer(s) may be fabricated from shape memory alloys (e.g., nickel titanium) that demonstrate stress-induced martensite at ambient temperature. Of course, other shape memory alloys may be used and the superelastic material may alternatively exhibit austenite properties at ambient temperature. The composition of the shape memory alloy may be chosen to produce the finish and start martensite transformation temperatures (Mf and Ms) and the start and finish austenite transformation temperatures (As and Af) depending on the desired material response and using the methods described herein. The superelastic/shape memory layer may be located along the full or a partial length or width of the patch/collar. If a superelastic material is used, FIG. 76*a* illustrates the patch 815 being in the deformed position and FIG. 76*b* illustrates the patch in the deployed position. If a shape memory material is used, FIG. 76*a* illustrates the patch 815 being in the cooled position and FIG. 76*b* illustrates the patch being in the transformed position after application of heat or exposure to body temperature.

When thermally forming the superelastic component layer 935 (FIG. 76), the superelastic material(s), which have been previously cut into the desired pattern and/or length, are stressed into the desired resting configuration over a mandrel or other forming fixture having the desired resting shape. The resting shape of the patch/collar depends on the vessel size or other location in which the patch/collar is intended to be used. After stressed into the restring configuration, the material is heated to between 300 and 650 degrees Celsius for a period of time, which is typically between 30 seconds and 30 minutes. Once the volume of superelastic material reaches the desired temperature, the superelastic material is quenched by inserting it into chilled water or other fluid, or otherwise allowing the material to return to ambient temperature. In this manner, the superelastic component layer(s) are fabricated into their resting configuration.

The hemostatic patch/collar may incorporate one or more therapeutic agents that positively affect healing at the site where the device is deployed, either incorporated into the structure forming the device, or incorporated into a coating, or both. Such therapeutic agents may include, but are not limited to, antithrombotics (such as anticoagulants), antimitogens, antimitotoxins, antisense oligonucleotides, gene therapy solutions, nitric oxide, and growth factors and inhibitors. Direct thrombin inhibitors that may be beneficial include Hirudin, Hirugen, Hirulog, PPACK (D-phenylalanyl-L-propyl-L-arginine chloromethyl ketone), Argatreban, and D-FPRCH.sub.2 Cl (D-phenylalanyl-L-propyl-L-arginyl chloromethyl ketone); indirect thrombin inhibitors include Heparin and Warfarin. Alternatively, a clot promoter may be used, such as protamine sulphate or calcium hydroxide.

Along with or in place of the adhesive used to adhere the patch/collar to the vessel, heat can be used as for the deployment/securing/bonding/healing process of the patch/collar. The heat can be used to recover the patch/collar, activate and cause a hemostatic material to flow to the puncture site, activate the shape memory/superelastic alloy component layer, activate a therapeutic substance, assist in sealing (e.g., by vessel collagen contraction), accelerate healing, or a combination of these or other effects.

Direct resistive element heating or ohmic tissue heating can be used to provide the heat (FIGS. 46 and 47). A biocompatible electrode material (e.g., gold, platinum, a combination of these or other suitable material) can be mixed with the patch/collar base material as a powder during compounding. Alternatively, strips, wires can be added onto any surface, or any layer of the patch or collar. Additionally, sputter coating, ion beam deposition, spraying, or adhesive bonding can be used to produce an electrode, and then be connected to a suitable wire conductor. For ohmic tissue heating, one conductor could be connected to an RF power source. Another conductor could be connected to a ground pad placed on the patient's body, and also connected to the power source. For direct resistive element heating, both conductors from the power source would be connected to the electrode. Once the puncture site has been sealed, the physician twists, cuts, or otherwise removes the conductor attached to the patch/collar. Alternatively, a special tip can be placed over a standard electro surgical tool (e.g., Bovie) to insert through the skin and make contact with the patch/collar and/or tissue.

The deployment device may have steering capabilities that are operable from the proximal end or side, such as by the thumb switch. The steering components may include one or more pull wires attached to a collar or thin shrink tube covered flat spring assembly or movable stylet. Alternatively, the deployment device can be positioned using a guide wire. The deployment device also or alternatively may contain sensors to confirm hemostasis, any other physical process, and/or provide diagnostic parameters. The sensors could include, but are not limited to, pressure transducers, Doppler, fluorescence, visualization sensors including ultrasonic, etc. The deployment device may have a grasping distal end, controllable from the proximal end or side of the device, and may be electrically conductive on the inside of the grasping ends, and used as a conductor (to make contact with the patch/collar and connected on the proximal end to the power source (through a wire or cable), or heating element, for direct resistive element heating, or ohmic tissue heating. The grasping end may also be designed to include electrode surfaces that controllably (from the proximal end) compress the cut or hole in the vessel, organ, or other, together, using heat to seal the tissue edges together. The deployment device also may be implemented as a catheter, cannula, trocar, introducer, or other device or instrument.

Versions of the deployment device may be modified to allow endoscopic, laparoscopic, or robotically-assisted based procedures. Similarly, a modified version of the device, system and method could be used for the closure of septal defects in the heart, as well as anywhere else in the body.

In general, the deployment device and patch/collar can be used for cardiovascular, gastrointestinal, neurological, reproductive, lymphatic, respiratory or other applications in which partial or complete, temporary or permanent closure, compression, sealing or reinforcement is desired. Additionally, the devices can be applied to any lumen, duct, organ, hollow body organs or cavity, or other structures or tissues, where partial or complete, temporary or permanent sealing, crimping, compression, plugging, reinforcement or other purpose is desired. Alternatively, the patch/collar device can be used as a conduit, conduit support and/or reinforcement by itself, or used with a synthetic and/or autogenous/autologous conduit or lumen. For conduit or conduit reinforcement applications, the material and design used would be sufficiently flexible, but resistant to kinking and or compressive closure. The hemostatic patch/collar also may be used completely or partially, outside, inside, in between, or in any combination with any lumen, vessel, duct, organ, hollow body organs, cavity, and or other structures or tissues within the body.

Like the patches described herein, the ACDs described herein may contain a metallic braid, coil, sheet, strip, wire, rod, or other configuration on the inner diameter, outer diameter, within, and/or a combination of these. The metallic material could be made from superelastic/shape memory alloys such as Nitinol. The metallic braid or coil could be annealed in one configuration during manufacture and processed and packaged in another configuration. When the material is exposed to normal body temperature (i.e., 37° C.), it will be set to either expand apart or contract inward depending on the design and annealed geometry (diameter). This characteristic may assist with the closure of the ACD.

It is important to understand basic terminology when describing metals with elastic, superelastic, or shape memory behavior. Elasticity is the ability of the metal, under a bending load, for example, to deflect (i.e., strain) and not take a permanent "set" when the load (i.e., stress) is removed. Common elastic metals can strain to about two percent before they set. Superelastic metals are unique in that they can withstand up to about ten percent strain before taking a set. This is attributed to a "stress-induced" phase change within the metal to allow it to withstand such dramatic levels of strain. Depending on the composition of the metal, this temperature that allows such a phase change can vary. And if the metal is "set" at one temperature, and then the temperature is changed, the metal can return to an "unset" shape. Then, upon returning to the previous "set" temperature, the shape changes back. This is a "shape-memory" effect due to the change in temperature changing the phase within the metal.

Elasticity is a key feature of superelastic materials. When a metal is loaded (i.e., stressed) and undergoes, for example, bending, it may deflect (i.e., strain) in a "springy" fashion and tend to return to its original shape when the load is removed, or it may tend to "set" and stay in a bent condition. This ability to return to the original shape is a measure of the elasticity or "resilience" of the metal. This ability for a metal to be resilient is desirable for such things as springs, shock absorbing devices, and even wire for orthodontic braces where the ability to deflect, but not deform (i.e., set) is important to maintain an applied force.

If, under a bending load, the metal takes a set, it is said to have plastically (versus elastically) deformed. This is because the imposed stress, produced by the bending load, has exceeded the "yield strength" (stress) of the metal. Technically, this level of stress that produces a set, is referred to as the "elastic limit", but is about the same as the yield strength. If the applied load increases past the yield strength of the metal, it will produce more plasticity and can eventually break. The higher the yield strength of the metal, the more elastic it is. "Good" elastic metals can accommodate up to about two percent strain prior to taking a set. But this is not the only factor governing "elasticity".

Another factor that determines the ability of a metal to deflect to a given, desired amount, but not take a set, is the "elastic modulus", or often called the modulus of elasticity. The modulus of the metal is an inherent property. Steels, for example, have a relatively high modulus (30 msi) while the more flexible aluminum has a lower modulus of about 10 msi. The modulus for titanium alloys is generally between 12 and 15 msi.

Resilience is the overall measure of elasticity or "spring-back ability" of a metal. The ratio of the yield strength divided by the modulus of the metal is the resilience. Although it is one thing for a metal to be resilient, it must also have sufficient strength for the intended service conditions.

As discussed above, when a metal is loaded, each increment of load (stress) produces a given increment of deflection (strain) within the metal. And the metal remains elastic if the applied is below the yield stress. However, there is a unique class of metal alloys that behave in an even more elastic manner. These are the "superelastic" metals, where, for a given applied stress (load) increment, the strain in the metal can reach 5 or 6 percent or more without taking a set. In these types of metals, the overall strain required to produce a set can reach an impressive 10 percent. This phenomenon is related to a phase change within the metal, and which is induced by the applied stress. This "stress-induced" phase change can also allow the metal to be set at one temperature and return to another shape at another temperature. This is a "shape-memory" effect, discussed below.

The most common superelastic metal, used in many commercial applications, is an alloy comprised of about equal parts of nickel (Ni) and titanium (Ti), and has a trade name of "Nitinol". It is also referred to as "NiTi". By slightly varying the ratios of the nickel and titanium in Nitinol, the stability of the internal phases in the metal can be changed. Basically, there are two phases: (1) an "austenite" phase and (2) a lower-temperature, "martensite" phase. When the metal is in an austenitic phase condition and is stressed, then a stress-induced martensite forms, resulting in the superelasticity. This is reversible, and the original shape returns upon release of the applied stress.

In general, the Ni-to-Ti ratio in the Nitinol is selected so that the stress-induced martensite forms at ambient temperatures for the case of super-elastic brace and support devices, which are used in ambient conditions. The specific composition can be selected to result in the desired temperature for the formation of the martensite phase (Ms) and the lower temperature (Mf) at which this transformation finishes. Both the Ms and Mf temperatures are below the temperature at which the austenite phase is stable (As and Af). The performance of an ACD can be further enhanced with the use of superelastic materials such as Nitinol. The superelasticity allows for greatly improved collapsibility, which will return to its intended original shape when the introducer (or catheter) is removed from the inside of the ACD. The high degree of flexibility is also more compatible with the stiffness of the engaged vessel.

By manipulating the composition of Nitinol, a variety of stress-induced superelastic properties can result, and over a desired, predetermined service temperature range. This allows the metal to behave in a "shape-memory" or "shape recovery" fashion. In this regard, the metal is "set" to a predetermined, desired shape at one temperature when in a martensitic condition, and which returns to the original shape when the temperature is returned to the austenitic temperature.

The shape memory phenomenon occurs from a reversible crystalline phase change between austenite and the lower-temperature martensite. In addition to this transformation occurring from an induced stress as described previously, it can, of course, also change with temperature variations. This transformation is reversible, but the temperatures at which these phase changes start and finish differs depending on whether it is heated or cooled. This difference is referred to as a hysteresis cycle. This cycle is characterized by the four temperatures mentioned previously, As, Af, Ms, and Mf. Upon heating from a lower-temperature martensite, the transformation to austenite begins at the As, and will be fully austenite at Af. And upon cooling, austenite will begin to transform back to martensite at the Ms temperature, and become fully martensitic at the Mf. Again, the specific composition of the alloy can result in a desired combination of these four transformation temperatures.

In the malleable martensitic state, the alloy can be easily deformed (set). Then upon heating back to the austenitic temperature, the alloy will freely recover back to its original shape. Then if cooled back to the martensitic state, the deformed shape reforms. The typical sequence of utilizing this shape memory property is to set the shape of, for example, a stent or anastomosis connector, while in the higher-temperature austenitic state. Then, when cooled, deform the martensite material, and then heat to recover the original shape.

Based on the background information provided above, it can be seen that if the Nitinol material requires an exceptionally tight bend, and one that would normally exceed the elastic limit of the material and thus permanently deform it, a bend can be placed in the device and the device annealed to relieve bending stresses within the device. Following this first bend, the device can be bent further to produce an even sharper bend, and then re-annealed to alleviate the stress from this additional bending. This process can be repeated to attain the desired, sharp bend or radii that would otherwise permanently deform the device if the bend were attempted in a single bending event. The process for recovery from the position of the most recent bend is then performed as described above.

Although the example of Nitinol, discussed above, is, by far the most popular of the superelastic metals, there are other alloys that can also exhibit superelastic or shape-memory behavior. These include the following:

Copper—40 at % Zinc

Copper—14 wt % Aluminum—4 wt % Nickel

Iron—32 wt % Manganese—6 wt % Silicon

Gold—5 to 50 at % Cadmium

Nickel—36 to 38 at % Aluminum

Iron—25 at % Platinum

Titanium—40 at % Nickel—10 at % Copper

Manganese—5 to 35 at % Copper

Titanium—49 to 51 at % Nickel (Nitinol)

Nitinol, because of the large amount of titanium in the composition, has been the only FDA approved superelastic/shape memory alloy for medical implant devices. The corrosion resistance of Nitinol is superior to that of commonly used 3161 stainless steel, and, if surface oxidized or passivated carefully, can reach corrosion resistance comparable to the most popular titanium implant alloy, Ti6Al4V. Similarly, the metal piece can be electropolished to improve its biocompatibility and blood compatibility. Biocompatibility studies have routinely showed Nitinol as a metal with suitable biocompatibility for medical device applications.

In summary, there are various ways of describing elasticity, but the main criterion is the ability of the metal to return to its initial, pre-loaded shape. Some metals can only deflect a couple percent and remain elastic while others, such as superelastic Nitinol, can deflect up to about ten percent. Nitinol is also biocompatible and corrosion resistant. This unique combination of properties allows a device made of Nitinol, such as an arterial closure device, to be fully collapsed within a deployment tool and be subsequently released, at a particular site within the vessel, to form its intended service shape.

Materials other than superelastic/shape memory alloys may be used as reinforcements provided they can be elastically deformed within the temperature, stress, and strain parameters required to maximize the elastic restoring force thereby enabling the tubular closure device to recover to a specific diameter and/or geometry once deployed inside, over, or on top of the vessel or other location. Such materials include other shape memory alloys, spring stainless steel 17-7, other spring metal alloys such as elgiloy™, inconel™, superelastic polymers, etc.

When thermally forming superelastic/shape memory reinforcements, the superelastic/shape memory material(s), previously cut into the desired pattern and/or length, are stressed into the desired resting configuration over a mandrel or other forming fixture having the desired resting shape of the tubular plug, depending on the vessel size or other location where the ACD or plug is intended to be used, and the material is heated to between 300 and 650° Celsius for a period of time, typically between 30 seconds and 30 minutes. Once the volume of superelastic material reaches the desired temperature, the superelastic material is quenched by inserting into chilled water or other fluid, or otherwise allowed to return to ambient temperature. As such, the superelastic reinforcements are fabricated into their resting configuration. The superelastic/shape memory reinforcements may be full or partial length or width of the ACD or tubular plug.

Any metal or metal alloy, such as a superelastic/shape memory alloy that comes in contact with blood and/or tissue can be electropolished. Electropolishing may reduce platelet adhesion causing thrombosis, and encourage endothelization of the exposed metallic areas. Electropolishing also beneficially removes or reduces flash and other artifacts from the fabrication of the device.

Superelastic/shape memory materials, such as tubular, rectangular, wire, braid, flat, round, combination or other structures also can be used in the design of the closure device, to assist with grasping, contacting, bringing tissue together, sealing, or other desired function. When used as a hollow conduit or reinforcement to a conduit, the superelastic/shape memory materials could be used to resist compressive closure and act as a flexible reinforcing strain relief to prevent kinking and to prevent the conduit from closing.

Numerous modifications and/or additions to the above-described embodiments and implementations are readily apparent to one skilled in the art. It is intended that the scope of the present embodiments and implementations extend to all such modifications and/or additions and that the scope of the present embodiments and implementations is limited solely by the claims.

For example, the engagement/contact section of the deployment tool can have a cross sectional geometry of a complete circle that may be designed to split away from the introducer once the closure device has been advanced/deployed. Splitting could be accomplished by having thinned or weakened areas in the wall of the deployment device tubing, such as linear perforations, or linear scores, combination, or other perforation configuration. This version would require that the deployment tool be back loaded onto the introducer before the closure device is placed onto the introducer and prior to insertion into the vessel.

The deployment tool can be a clip-on tool, can compress the device to reduce the cross sectional profile prior to insertion and/or may include a constraining sheath to reduce a section, or sections of the device during insertion to the target site. This version would be particularly useful for bringing two tissue walls together while yet providing a conduit between the tissues.

The proximal end of the ACDs described herein may be closed using hemostats, or other tools, by pinching the end together until the inner diameter bonds, or compresses together. Adhesive may be used to assist in the closure of the device.

The proximal edge of the closure device and the distal (or other) edge of the advancement/deployment tool can have interlocking geometries to aid control during advancement (particularly when inserting by twisting or turning while advancing into the vessel).

The proximal edge or end of the closure device may have a collar made of a superelastic/shape memory material, an elastic combination of materials or suitable elastic materials that would compress the end of the device together once the introducer is removed from the inner diameter of the closure device. As previously mentioned, the closing and sealing of the device may be enhanced with an adhesive, swellable material, or other coating or layer.

The closure means can be other than a tubular structure, such as a plug. A special introducer, having multi-lumens, one for the catheter or other device, and at least one for the hemostatic plug material. The hemostatic material, and matching geometry plunger would be inserted into the proximal end of the special introducer. As the plunger is advanced, the hemostatic material is advanced into position and the introducer is withdrawn from the vessel.

The basic device, system and method can be sized and configured for medical devices other than vascular introducers, such as guide wires, catheters, laparoscope, endoscope, trocar, cannula, electrode wire, or other.

Using the tubular closure device, especially when made from swellable material, as a reversible sterilization method for women by occluding the fallopian tubes, and men by occluding the vas ducts or tubes.

A modified version of the device and system can be used for the closure of septal defects in the heart, as well as anywhere else in the body. For this, as well as other additional applications, the clip on section of the deployment tool would be modified to fit onto the catheter, and be long enough (such as, e.g., full catheter length) to be remotely advanced from the proximal end of the catheter. The deployment tool also may be modified and used to compress the device during insertion into the body to thereby reduce the cross-sectional profile during insertion. The deployment method may be enabled by longitudinal movement, manipulation, or retraction of the deployment tool away from the closure device, which removes the compression of the device and allows the device to expand and fill in the opening, such as a septal defect.

The ACDs described herein can be used for cardiovascular applications where hemostasis (temporary or permanent) is desired. Additionally, the ACDs can be used with simple modifications for any tubular, duct, organ, hollow body cavity, or other structures or tissues, where temporary or permanent sealing or plugging is needed, or alternatively, where a conduit or conduit reinforcement is desired. For conduit or conduit reinforcement applications, the material and design used thereby would be sufficiently resistant to compressive closure while still remaining flexible, e.g., longitudinally and/or radially flexible. One or more of the patches/collars can be placed on or near the left ventricle to treat congestive heart failure ("CHF") by preventing, delaying, or limiting remodeling and to assist the left ventricle to decompress during systole based on the superelastic/shape memory properties of the metal alloy within the patch/collar. In general, the device is placed to constrain the outside of the heart without significantly interfering with the normal movement or function of the heart to prevent remodeling of the heart tissue. In this manner, the device assists the ventricular contraction of the heart by providing a device that, when deflected outward, will tend to return to the as-annealed configuration of the superelastic/shape memory reinforcing member contained on or inside the device. The device can be fabricated from single or multiple strips or bands. To be as atraumatic as possible, the strips or bands can be fabricated with rounded ends.

Figure 77A:
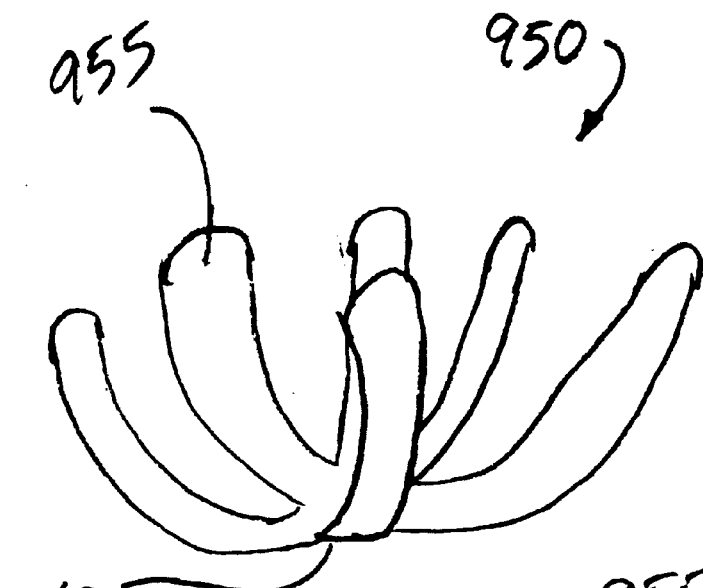
FIGS. 77a–c illustrate a congestive heart failure device based on the patch/collar.
Figure 77B:
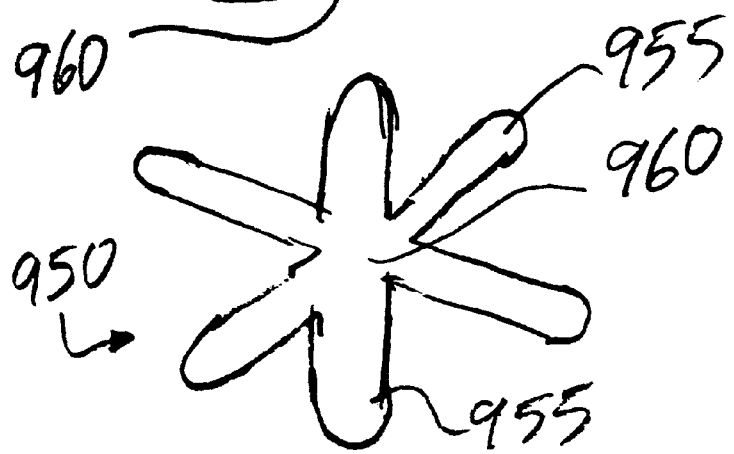
Figure 77C:
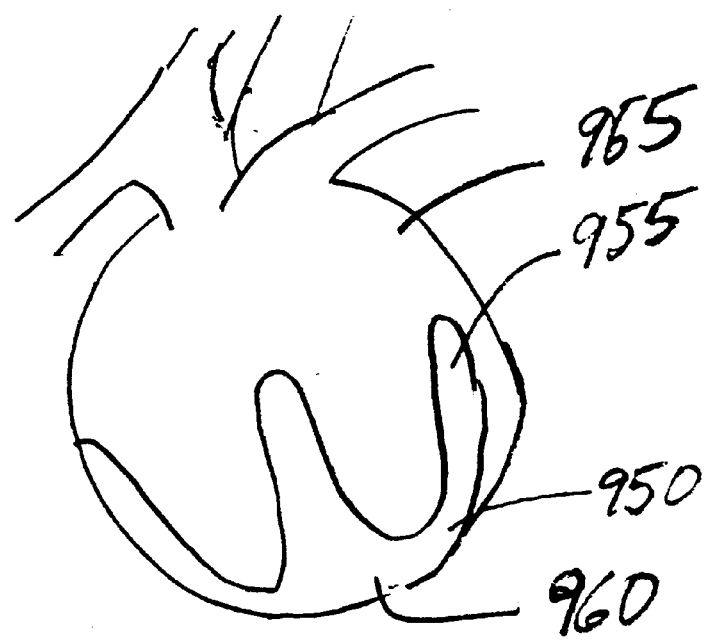

Referring to FIGS. 77a–77c, a CHF device 950 can be configured in a generally star pattern that includes arms 955 and a base 960. The device 950 is positioned on a heart 965 in a centered manner on the bottom apex of the heart. Of course, the device 950 can be centered on other locations of the heart 965, such as the left ventricle and/or the right ventricle, such that the device resists remodeling while nonetheless assisting the heart to attain systole.

The device 950 can include an atraumatic tissue contacting surface (e.g., such as ePTFE or woven Dacron) that may optionally be provided with an adhesive on or near the tissue contacting surface. The device may include one or more layers (e.g., in the form of a strip, band, wire, tube, rod, mesh) of superelastic/shape memory material, or other reinforcing material as previously disclosed herein. The superelastic/shape memory material may be annealed in any configuration as required or desired such that when deflected or forced from its as annealed configuration, it will have a tendency to return to its annealed configuration. Multiple strips or strip ends may be independent, or attached to one another or a combination of both. The ends may be attached to each other by using a mesh, single or multiple strips, bands, wires, and/or tubes. The attachment(s) may be elastic, semi elastic, rigid, or have a combination of these properties. The attachment may be made by using any of the methods described herein or using any commonly known technique. The rigidity, flexibility, closure compressive force of the device 950 may be modified by varying, for example, the device's geometry, thickness, material, component(s), or processing.

The device may be positioned against the heart by using instrument or manipulating the device by hand. Sutures, adhesives, barbs, or a combination of these or other retaining methods may be used, as detailed herein.

Figure 78A:
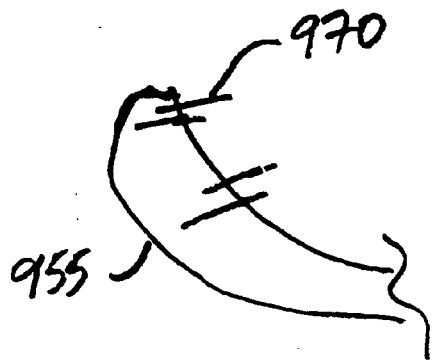
FIGS. 78a and 78b illustrate an arm of the congestive heart failure device of FIG. 77a having retaining barbs.
Figure 78B:
Figure 79:
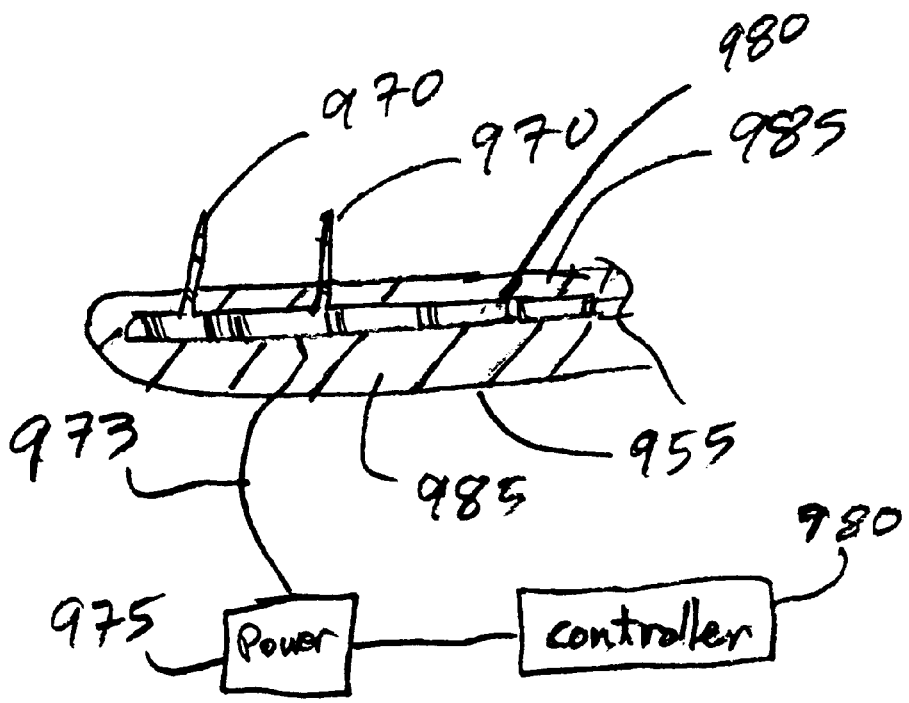
FIG. 79 illustrates a technique for applying heat to the barbs of FIG. 78a to form channels in the heart to which the device is congestive heart failure device is applied.

Referring to FIGS. 78a and 78b, the device 950 can include barbs 970 extending from the arms 955 and/or base 960. The barbs 970 can be oriented to retain the device against the heart. For example, the barbs 970 can extend directly from the arm 955 or base 960 (FIG. 78a) or at an angle from the arm or base (FIG. 78b). Referring also to FIG. 79, the arms 955, base 960, and barbs 970 can be electrically connected by a wire 973 to a power source 975 and controller 980 to apply or supply heat to the barbs. The arms include the superelastic/shape memory material 980 and an outer layer of insulative, biocompatible polymer 985. By applying heat to the barbs 970 once the device 950 is implanted against the heart will cause the barbs to heat the tissue through which they pass. In addition to securing the patch to the tissue surface, this attachment method is believed and intended to provide an effect that is similar to transmyocardial revascularization.

The ACDs described herein also can be used for pulmonary and respiratory applications, gastric bypass procedures, a gastric band, general tissue bunching or 5 bringing tissues together, and/on or in other vessels, organs, tissues, bones, and/or other body tissues than those specifically described.

The ACD and patches/collars also can be used for cardiovascular, gastrointestinal, neurological, reproductive, lymphatic, respiratory or other applications where partial or complete, temporary or permanent closure, compression, sealing or reinforcement is desired. Additionally, any lumen, duct, organ, hollow body organs or cavity, or other structures or tissues, where partial or complete, temporary or permanent sealing, crimping, compression, plugging, reinforcement or other purpose is desired.

While several particular forms of the invention have been illustrated and described, it will be apparent that various modifications and combinations of the invention detailed in the text and drawings can be made without departing from the spirit and scope of the invention. For example, references to materials of construction, methods of construction, specific dimensions, shapes, utilities or applications are also not intended to be limiting in any manner and other materials and dimensions could be substituted and remain within the spirit and scope of the invention. Accordingly, it is not intended that the invention be limited, except as by the appended claims.

What is claimed is:

1. A patch for placing against a tissue within a mammalian, the patch comprising:

at least one layer of a biocompatible polymer;

at least one layer of a biocompatible superelastic/shape memory material; and at least one layer of a biocompatible adherent material.

2. The patch of claim 1, wherein the superelastic/shape memory material comprises a nickel titanium alloy.

3. The patch of claim 2, wherein the alloy comprises Nitinol.

4. The patch of claim 1, wherein the superelastic/shape memory material has a curved configuration in a resting state.

5. The patch of claim 1, further comprising barbs extending from the superelastic/shape memory material.

6. The patch of claim 5, further comprising a power source connected to the patch and configured to provide power to the barbs.

7. The patch of claim 1, wherein the layer of superelastic/shape memory material is encapsulated by the polymer.

8. The patch of claim 1, wherein the patch is intended to close an opening in the vessel.

9. The patch of claim 1, wherein the patch comprises multiple arms and a base configured to form a concave shape.

10. The patch of claim 9, further comprising one or more barbs extending from the arms.

11. The patch of claim 1, further comprising a deployment device configured to deploy the patch, the deployment device comprising a handle and a deployment section, the deployment section configured to retain the patch for delivery of the patch to the vessel.

12. The patch of claim 11, wherein the deployment section includes a pair of openable jaws.

13. The patch of claim 11, wherein the deployment section includes a surface configured to apply a vacuum.

14. A method of applying a patch to a tissue surface within a mammalian body, the method comprising:

retaining the patch to a deployment device;

advancing the deployment device to the tissue surface;

pressing the patch against the tissue surface; and manipulating the deployment device to separate the deployment device from the patch and leave the patch against the tissue surface, wherein the patch comprises at least one layer of a biocompatible polymer, at least one layer of a biocompatible superelastic/shape memory material; and at least one layer of a biocompatible adherent material, and the deployment device comprises a handle section and a deployment section, the deployment section configured to retain the patch for delivery of the patch to the tissue surface.

15. The method of claim 14, wherein retaining the patch to the deployment device comprises using an adhesive to retain the patch to the deployment device.

16. The method of claim 14, wherein retaining the patch to the deployment device comprises applying vacuum to the patch.

17. The method of claim 14, wherein manipulating the deployment device to separate the deployment device from the patch comprises moving the deployment device relative to the tissue surface to which the patch is applied.

18. The method of claim 14, wherein manipulating the deployment device to separate the deployment device from the patch comprises advancing a plunger within the deployment device.

19. The method of claim 14, wherein manipulating the deployment device to separate the deployment device from the patch comprises opening a pair of jaws in the deployment section.

20. The method of claim 14, wherein the patch comprises one or more arms, a base, and barbs extending from the arms, and advancing the deployment device to the tissue surface comprises advancing the deployment device to the tissue surface of the heart.

* * * * *